(12) United States Patent
Lee et al.

(10) Patent No.: US 7,951,779 B2
(45) Date of Patent: May 31, 2011

(54) METHOD OF PROTECTING CELLS AGAINST DAMAGE AND PHARMACEUTICAL COMPOSITION COMPRISING LEUMORPHIN

(75) Inventors: Byoung Dae Lee, Pohang (KR); SooMi Kim, Pohang (KR); Eun-Mi Hur, Pohang (KR); Yong-Soo Park, Pohang (KR); Yun-Hee Kim, Pohang (KR); Taehoon Lee, Pohang (KR); Kyong-Tai Kim, Pohang (KR); Pann-Ghill Suh, Pohang (KR); Sung Ho Ryu, Pohang (KR)

(73) Assignees: Postech Academy-Industry Foundation, Pohang, Kyungsangbuk-Do (KR); Postech Foundation, Pohang, Kyungsangbuk-Do (KR)

( * ) Notice: Subject to any disclaimer, the term of this patent is extended or adjusted under 35 U.S.C. 154(b) by 58 days.

(21) Appl. No.: 11/482,480

(22) Filed: Jul. 6, 2006

(65) Prior Publication Data

US 2007/0010451 A1   Jan. 11, 2007

Related U.S. Application Data

(60) Provisional application No. 60/595,459, filed on Jul. 7, 2005.

(51) Int. Cl.
*A61K 38/33*   (2006.01)

(52) U.S. Cl. ...... 514/18.9; 514/1.4; 514/15.1; 514/16.4; 514/18.2

(58) Field of Classification Search ........................ None
See application file for complete search history.

(56) References Cited

U.S. PATENT DOCUMENTS 5,475,019 A * 12/1995 Privette et al. ................ 514/408

OTHER PUBLICATIONS

The Merck Manuals Online Medical Library, [online]. Whitehouse Station, NJ: Merck Research Laboratories, 2006-2007. [retrieved on Oct. 25, 2007]. Retrieved from the Internet: < URL: http://www.merck.com/mmpe/print/sec16/ch213/ch213c.html >. Dementia, pp. 1-18.*
Marsh International Review of Psychiatry 2000, 12:307-318.*
Teri et al. Journal of Gerontology: Medical Sciences 1999, 54:M348-352.*
Warshaw et al. The American Journal of Psychiatry 1993, 150:1512-1516.*
Misell et al. Breast Cancer Reasrch and Treatment 2005 89:257-264.*

* cited by examiner

*Primary Examiner* — Sharon Wen
(74) *Attorney, Agent, or Firm* — JHK Law; Joseph Hyosuk Kim

(57) ABSTRACT

The present invention relates to a method of protecting cells against damage caused at least in part by apoptosis, comprising administering to subjects a therapeutic dose of leumorphin having cytoprotective activity, and a pharmaceutical composition comprising an effective amount of leumorphin having a cytoprotective activity.

3 Claims, 15 Drawing Sheets

SEQUENCE LISTING

<160> NUMBER OF SEQ ID NOS: 2

<210> SEQ ID NO 1
<211> LENGTH: 29
<212> TYPE: PRT
<213> ORGANISM: Sus scrofa

<400> SEQUENCE: 1

Tyr Gly Gly Phe Leu Arg Arg Gln Phe Lys Val Val Thr Arg Ser Gln
1               5                   10                  15

Glu Asp Pro Asn Ala Tyr Ser Gly Glu Leu Phe Asp Ala
            20                  25

```
<210> SEQ ID NO 2
<211> LENGTH: 28
<212> TYPE: PRT
<213> ORGANISM: Rattus sp.

<400> SEQUENCE: 2

Tyr Gly Gly Phe Leu Arg Arg Gln Phe Lys Val Val Thr Arg Ser Gln
1               5                   10                  15

Glu Asn Pro Asn Thr Tyr Ser Glu Asp Leu Asp Val
            20                  25
```

METHOD OF PROTECTING CELLS AGAINST DAMAGE AND PHARMACEUTICAL COMPOSITION COMPRISING LEUMORPHIN

CROSS-REFERENCE TO RELATED APPLICATION

This application claims priority to and the benefit of U.S. provisional patent application No. 60/595,459 filed in the United State of America Patent & Trademark Office on Jul. 7, 2005, the entire contents of which are incorporated herein by reference.

BACKGROUND OF THE INVENTION (a) Field of the Invention The present invention relates to a method of protecting cells against damage caused at least in part by apoptosis, comprising administering to subjects a therapeutic dose of leumorphin having cytoprotective activity, and a pharmaceutical composition comprising an effective amount of leumorphin having a cytoprotective activity.

(b) Description of the Related Art

Endogenous opioid peptides, found in the central and peripheral nervous systems, play important roles in a wide variety of physiological and pathophysiological conditions. Multiple peptides are derived from their precursors, proopiomelanocortin, proenkephalin and prodynorphin, through hydrolysis by proteases.

Prodynorphin undergoes endoproteolysis at specific sites, which results in the generation of leumorphin, neoendorphin, rimorphin (dynorphin B) and dynorphin (dynorphin A) (Waldhoer et al., 2004). Dynorphin A, the most abundant form of dynorphins, has been shown to be involved in a range of functions, and activation of the κ-opioid receptor (KOR) accounts for many of its biological activities (Solbrig and Koob, 2004).

The pharmacological and functional properties of other prodynorphin gene products, however, have been characterized to a much lesser extent. It has been reported that leumorphin can be further processed and converted to rimorphin by endopeptidases (Berman et al., 1995), but leumorphin and rimorphin have comparable affinities for the KOR, implying that further processing may not be necessary to achieve maximal affinity and activity (Mansour et al., 1995). Although there are multiple products processed from a single gene, functional diversity of the peptides has not been clearly elucidated (Suda et al., 1983a; Mansour et al., 1995).

Increasing pharmacological and biochemical evidence suggests that various responses mediated by the opioid peptides cannot entirely be explained by activation of opioid receptors (Wollemann and Benyhe, 2004). Peptides exhibiting the so-called "non-opioid" effects include β-endorphin (Navolotskaya et al., 2002), dynorphin (Walker et al., 1982), nociceptin (Mollereau et al., 1996) and Met-enkephalin (Zagon et al., 1991). Classical pharmacological definition of opioid actions involves the antagonism of their effects by naloxone, a general antagonist of the opioid receptors, whereas the non-opioid actions are insensitive to naloxone. Existence of these non-opioid actions might provide an explanation for the diverse and complex pharmacological and physiological properties elicited by opioid peptides in vivo.

Opioids produce strong analgesic effects in animals. In addition to these well-recognized effects, increasing evidence suggest that opioids elicit a variety of biological responses that appear to be independent of their analgesic properties, but may rather have effects on cell survival and proliferation (Dermitzaki et al., 2000; Tegeder and Geisslinger, 2004). These effects have been suggested to involve activation of protein kinase B (AKT) and/or extracellular signal-related protein kinase (ERK) signaling pathways. Some of the observed effects have been suggested to be downstream of opioid receptors (Polakiewicz et al., 1998; Persson et al., 2003), whereas others have been shown to be insensitive to opioid receptor antagonists or pertussis toxin (Moon, 1988; Tegeder and Geisslinger, 2004), implying that some of the effects might be independent of opioid receptor activation. It is still unclear whether these responses are mediated through activation of typical opioid receptors and inhibitory G-protein-signaling.

Although many distinct endogenous opioid peptides have been identified, it has not been clearly demonstrated so far whether the products of prodynorphin exhibit functional and pharmacological diversity. In order to address this issue, we examined the effects of endogenous opioid peptides derived from prodynorphin on intracellular signaling events and cell viability in rat pheochromocytoma PC12 cells that express and secret prodynorphin as well as its cleaved products (Margioris et al., 1992).

SUMMARY OF THE INVENTION

It is an object of this invention to provide a method of protecting cells against damage caused at least in part by apoptosis, comprising administering to subjects a therapeutic dose of leumorphin having cytoprotective activity. The leumorphin activates epidermal growth factor receptor kinase (ERK) and a protein kinase B (AKT).

In one embodiment of the invention, a method of preventing or alleviating damage associated at least in part with apoptosis is provided. In a related aspect of this embodiment, a method of treating subjects at risk for cell damage associated at least in part with apoptosis is provided. These subjects include patients at risk of damage to blood vessels or tissue in various organs caused, at least in part, by apoptosis. At risk patients include, for example, those suffering (severe) sepsis, ischemia/reperfusion injury, ischemic stroke, acute myocardial infarction, acute or chronic neurodegenerative diseases, or those undergoing organ transplantation or chemotherapy, among other conditions.

In another embodiment of the invention, a pharmaceutical composition comprising an effective amount of leumorphin having a cytoprotective activity is provided. The composition further comprises a pharmaceutically acceptable carrier, exipient, or diluent.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawing.

DETAILED DESCRIPTION OF THE EMBODIMENTS

Figure 1A:
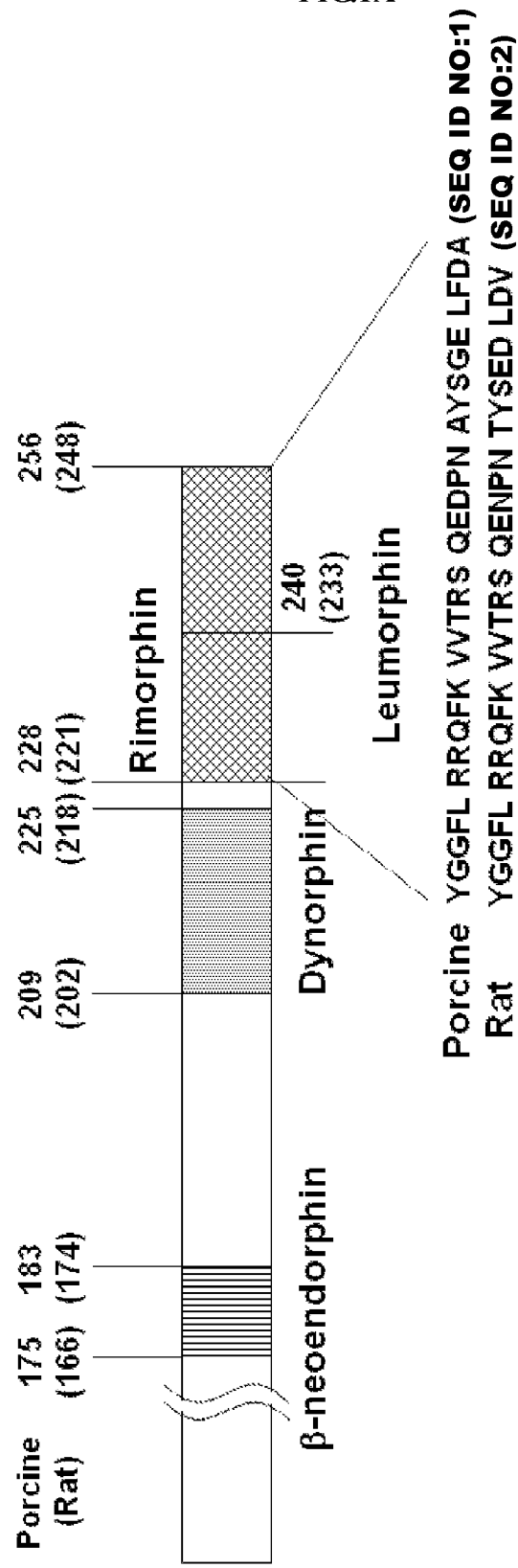
FIG. 1A to 1E show Effects of prodynorphin gene products on cell survival in PC12 cells.

An exemplary embodiment of the present invention will hereinafter be described in detail with reference to the accompanying drawings.

The present invention provides evidence that leumorphin exerts a specific anti-apoptotic effect, which is mediated by activation of c-Src and epidermal growth factor receptor (EGFR) kinases. Interestingly, this effect was not manifested by any of the other prodynorphin gene products and was insensitive to antagonists of opioid receptors, suggesting that leumorphin has a novel function independent of KOR activation.

Endogenous opioid peptides, found in the central and peripheral nervous systems, perform neuromodulatory roles, and display a wide diversity of functional and pharmacological properties both in vitro and in vivo. In the present invention, the effects of prodynorphin gene products on intracellular signaling events and cell survival in rat pheochromocytoma PC12 cells are investigated. Leumorphin, but not other prodynorphin gene products including dynorphin A, neoendorphin, and rimorphin (dynorphin B), increased cell viability in PC12 cells. The cytoprotective effect of leumorphin is dependent on the PI3-Kinase and MAPK pathways, but is insensitive to both naloxone, a general antagonist of the opioid receptor, and nor-binaltorphimine, a specific antagonist of the kappa opioid receptor (KOR). Moreover, competition binding assay clearly reveals that leumorphin had another binding site(s) in addition to that for the KOR. Interestingly, leumorphin induced activation of the epidermal growth factor receptor (EGFR) through a Src-dependent mechanism, which is proved to be responsible for the increased survival response. Flow cytometric and microscopic analysis shows that leumorphin rescued cells from serum deprivation-induced apoptosis. Collectively, it is suggested that leumorphin prevents apoptosis via EGFR-mediated activation of the PI3-Kinase and MAPK pathways, which occur independent of the KOR.

The present invention reveals a novel function of leumorphin in the regulation of cell survival. This function is mediated by AKT and ERK signaling pathways, but appears to be independent of activation of the KOR. Our conclusion is supported by three independent experimental results. Firstly, leumorphin induced phosphorylation of AKT and ERK, and the cytoprotective effect of leumorphin was inhibited by LY294002, wortmannin, PD98059, and U0126 (FIG. 4E). Interestingly, none of these effects were elicited by any other agonists of the KOR, including dynorphin, rimorphin, β-neoendorphin, and (−)-U-50488 (FIG. 1 and FIG. 4). Furthermore, leumorphin is capable of inducing phosphorylation of both AKT and ERK in HEK-293 cells that do not express the KOR (data not shown). Secondly, these effects are insensitive to the antagonists of opioid receptors, naloxone and nor-BNI (FIG. 2 and FIG. 4). Thirdly, the effect of leumorphin was unaffected by PTX, which inhibits the $G\alpha_{i/o}$ superfamily of G proteins associated with the KOR (FIG. 2). Our study is the first demonstration of suggesting that leumorphin has a cytoprotective effect, insensitive to opioid receptor antagonists.

The PC12 cell line has been extensively used as an in vitro model for the study of adrenal chromaffin cell function, proliferation, apoptosis, and differentiation to neural cells. It has been reported that PC12 cells produce prodynorphin gene products (Yoshimasa et al., 1981; Suda et al., 1983b) and respond to them. PC12 cells express the classical ☐δ-, μ-, and κ-opioid membrane receptors (Kampa et al., 1999; Dermitzaki et al., 2000; Yoshikawa et al., 2001), which account for many of the biological responses of the opioid peptides. In this report, we show that the prodynorphin gene product, leumorphin but not dynorphin and rimorphin has a long-lasting anti-apoptotic effect in PC12 cells. As shown in FIG. 1 and FIG. 4, rimorphin is a C-terminal deleted form of leumorphin, but it does not have similar effects as leumorphin, implicating that the C-terminal portion of leumorphin (14-29) might be important for the novel function of leumorphin.

Figure 3:
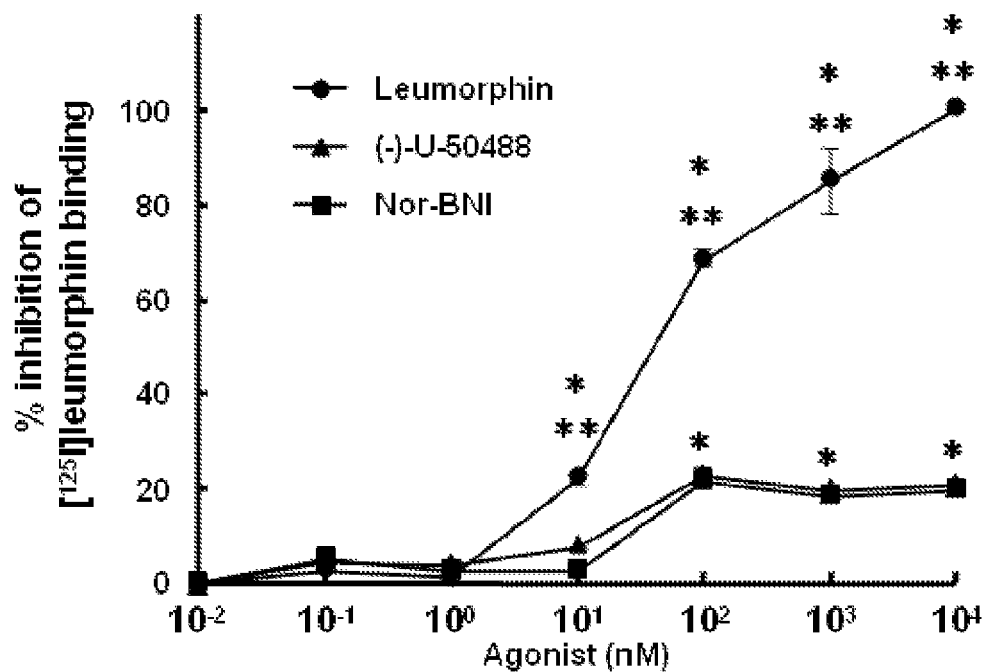
FIG. 3 shows an inhibition of [$^{125}$I]leumorphin binding in PC12 cells. PC12 cells were treated with various concentrations of unlabeled leumorphin, (−)-U-50488 and nor-BNI in the presence of $^{125}$I-labeled leumorphin (25 pM) for 3 hr at 4° C.

However, when the properties of various N-terminal fragments of leumorphin are tested, none of the peptides have any effects (unpublished data). Therefore, it is suggested that the novel functions of leumorphin may be derived from the intact form of leumorphin. Both leumorphin and dynorphin can bind to KOR (Suda et al., 1983a; Mansour et al., 1995). Our results, however, suggest that leumorphin has another binding site(s), in addition to that for the KOR in PC12 cells (FIG. 3). A specific agonist and antagonist of the KOR only partially competed out for labeled leumorphin, and their effects were saturated at 100 nM, which corresponds to the binding affinity to KOR. To the contrary, the extent of inhibition elicited by cold leumorphin continued to increase up to 10 μM. These results highly correlate with the concentration profiles of the functional properties and signaling events triggered by leumorphin but not other KOR agonists demonstrated in the present study.

Increasing evidence reveals that there are many exceptions, both in functional and pharmacological aspects, to the expected antagonism of the effects of opioid peptides by naloxone (Arendt et al., 1995; Gupta et al., 2002). Furthermore, there is an obvious disparity between existence of only three classical opioid receptor genes and the substantial evidence for additional pharmacological and functional phenotypes (Waldhoer et al., 2004). Therefore, posttranslational modifications and homo/heterooligomerization of the existing receptor proteins, or presence of novel opioid receptors might provide an explanation for the observed diversity and nonresponsiveness to opioid receptor antagonists.

The cytoprotective effect of leumorphin is insensitive to naloxone, excluding the three types of the classical opioid receptors. However, the ε-type receptor, a non-classical opioid receptor, is insensitive to naloxone and has low affinity to dynorphin and U-50488 (Nock et al., 1990). Interestingly, the pharmacological properties of leumorphin to trigger signaling pathway and rescue cells from apoptosis are reminiscent of those of the ε-type receptor. We, therefore, examined the effect of β-endorphin, an agonist of the ε-type receptor, on phosphorylation of AKT and ERK. However, neither AKT nor ERK was phosphorylated in response to β-endorphin treatment (data not shown), excluding the involvement of the ε-type receptor. In order to define the non-opioid receptor responsible for the specific functions of leumorphin, we investigated the possible involvement of other known GPCRs that share sequence homology with opioid receptors. For this purpose, we examined involvement of the opioid receptor-like protein (NOP), which has approximately 60% sequence homology with opioid receptors (Connor and Christie, 1999). However, the NOP antagonist, UFP-101, did not have any effect on leumorphin-induced phosphorylation of AKT and ERK (data not shown). We also examined the possible involvement of other receptors which have varying degrees of sequence homology (20-30% homology) with the opioid receptors, including receptors for somatostatin, angiotensin, formyl methionylleucylphenylalanine, neuropeptide Y and interleukin-8 (Minami and Satoh, 1995). However, none of the tested agonists of these receptors mimicked functions of leumorphin (data not shown).

We suggest that the anti-apoptotic effect of leumorphin is mediated via Src-dependent activation of the EGFR (FIG. 5). Recent studies have revealed that activation of EGFR is responsible for the proliferative and anti-apoptotic effects of various unrelated receptors, many of which are GPCRs (Fischer et al., 2003). Src-family tyrosine kinases have been suggested to be an upstream mediator of EGFR activation induced by many GPCRs (Luttrell et al., 1997). In this report, the function of leumorphin was attenuated by a specific EGFR kinase inhibitor, AG1478 and a Src kinase inhibitor, PP2 as well as by overexpression of kinase-defective mutant of c-Src. In addition, leumorphin-induced increase of EGFR tyrosine phosphorylation was inhibited by PP2. In this report, we did not identify the receptor responsible for the novel function of leumorphin, but our data are reminiscent of the typical results from EGFR transactivation induced by GPCR. Further studies are required for characterization and identification of this unknown receptor for leumorphin.

There are controversial reports about the role of dynorphin in apoptosis and cytotoxicity in PC12 and other neuronal cells. It has been suggested that dynorphin has a transient anti-apoptotic function in PC12 cells (Dermitzaki et al., 2000). However, some other reports suggest that dynorphin induces apoptosis in striatal neurons (Singh et al., 2003) and induces cytotoxicity in neuroblastoma-glioma hybrid NG108-15 cells (Tan-No et al., 2001). However, the pro-apoptotic nor the anti-apoptotic effect of dynorphin was observed in our system. This might have been resulted from the method that we applied to induce cell death. Serum deprivation is a potent inducer of apoptosis, a condition in which the effect of dynorphin might hardly be distinguished. An alternative explanation can be that the effect of dynorphin might have been obscured by the endogenous prodynorphin peptides expressed and secreted from PC12 cells.

A recent study reported that brain injury and inflammation enhances the expression of *prodynorphin* mRNA as well as the secretion of opioid peptides (Cabot et al., 2001; Redell et al., 2003), implicating that the release of opioid peptides might be increased in pathophysiological conditions. The secreted opioid peptides have important roles in reducing pain at the site of tissue injury, which are their well-known primitive analgesic effects. In this study, we propose that leumorphin might perform an important role in the regulation of cell viability under pathophysiological conditions, such as neuronal dysfunctions and tissue damage, thereby counteracting cytotoxicity, which would work in concert to overcome tissue injury. Therefore, it is plausible to suggest that the release of different opioid peptides can be orchestrated in a desired fashion in an effort to accomplish biological roles in vivo.

In conclusion, our present findings reveal a novel function of leumorphin. It is interesting that leumorphin can function as a neurotransmitter/neuromodulator through activation of the classical KOR and can also regulate cell survival through activation of a totally different, as yet unidentified receptor. The novel function of leumorphin demonstrated in our study might provide a further explanation for the neuroprotective effects of prodynorphin gene products in physiological and pathological conditions.

In another embodiment of the invention, a pharmaceutical composition comprising an effective amount of leumorphin having a cytoprotective activity is provided. The composition further comprises a pharmaceutically acceptable carrier, exipient, or diluent.

Dosage forms of a pharmaceutical composition of the present invention or its respective active ingredients include oral dosage forms such as tablets, capsules (including soft capsules and microcapsules), powders, granules, syrups, and etc.; and non-oral dosage forms such as injections (e.g., subcutaneous injections, intravenous injections, intramuscular injections, intraperitoneal injections, etc.), external application forms (e.g., nasal spray preparations, transdermal preparations, ointments, etc.), suppositories (e.g., rectal suppositories, vaginal suppositories, etc.), pellets, drip infusions, and etc.

The dosage of a pharmaceutical composition of the present invention may be appropriately determined with reference to the dosage recommended for the respective drug(s), and can be selected appropriately according to the subject, the age and body weight of the subject, current clinical status, administration time, dosage form, method of administration, combination of the drug(s), and etc.

The present invention is further explained in more detail with reference to the following examples. These examples, however, should not be interpreted as limiting the scope of the present invention in any manner.

EXAMPLE

Method and Materials

MATERIALS: Rat pheochromocytoma PC12 cells were purchased from ATCC (Manassas, Va.). RPMI 1640 was from Life Technologies, Inc. (Gaithersburg, Mass.). Bovine calf serum (BCS) and equine serum (ES) were from HyClone (Logan, Utah). β-neoendorphin, dynorphin, leumorphin, and rimorphin were obtained from BioChem (Bubendorf, Switzerland). (−)-U-50488, D-Phe-Cys-Tyr-D-Trp-Om-Thr-Pen-Thr-NH2 (CTOP), and nor-binaltorphimine dihydrochloride (nor-BNI) were from Tocris Cookson Ltd. (Avonmouth, UK). [125I]leumorphin was from Phoenix Pharmaceuticals, Inc. (Belmont, USA). [4-(3-chloroanilino)-6,7-dimethylquinoaline hydrochloride (AG1478), [2'-amino-3'-methoxyflavone (PD98059), [2-(4-morpholinyl)-8-phenyl-4H-1-benzopyran-4-one] (LY294002), Wortmannin, U0126, and {4-amino-5-(4-chlorophenyl)-7-(t-butyl)pyrazolo[3,4-d]pyrimidine (PP2) were from Calbiochem (La Jolla, Calif.). Phospho-p44/42 MAP kinase (Thr202/Thr204) antibody, p44/42 MAP kinase antibody, and AKT antibody were from Cell Signaling Technology Inc. (Beverly, Mass.). Anti-phospho-AKT (Ser473) antibody and 3-(4,5-dimethylthiazol-2-yl)-2,5-diphenyltetrazolium bromide (MTT) were purchased from Sigma (St. Louis, Mo.). Anti-EGFR antibody was from Upstate (Lake Placid, N.Y.). Peroxidase-conjugated anti-sheep, anti-rabbit and anti-mouse IgG were from Kirkegaard and Perry laboratories Inc. (Gaithersburg, Mass.). TUNEL assay kit was purchased from Promega Corp. (Madison, USA).

Cell Culture

PC12 cells were maintained in RPMI 1640, supplemented with 10% (v/v) BCS and 5% (v/v) ES. The cells were grown at 37° C. in a humidified atmosphere of 5% CO2 and 95% air.

Plasmid and Transfection

The cDNA encoding a kinase-defective, dominant inhibitory form of Src (SrcK298M) was cloned into mammalian expression vector pME-18S, and PC12 cells were transiently transfected with expression vectors by electroporation (Hur et al., 2004). In some experiments, cells were co-transfected with an expression vector for green fluorescent protein (Clontech, Franklin Lakes, N.J.), and positive clones were identified under fluorescence microscopy to compare the transfection efficiencies between experiments.

MTT Conversion Assay

The assay was performed as previously described (Mosmann, 1983). PC12 cells were seeded at a density of $1 \times 10^5$ cells/well into a 24-well plate and cultured for 24 hr. For serum deprivation, we changed maintaining medium to serum free medium and cells were cultured for appropriate time as indicated. MTT was dissolved in phosphate-buffered saline (PBS) at a concentration of 5 mg/ml. The stock solution was filtered and added to the culture medium to a final concentration of 500 µg/ml. The plates were incubated at 37° C. for 2 hr. Dark brown formazan crystals formed after reduction of the tetrazolium ring by the mitochondria of living cells. The crystals were dissolved in DMSO, and the optical densities of the samples were measured at 570 nm.

cAMP Measurement

Intracellular cAMP generation was determined by [$^3$H] cAMP competition assay as previously described (Suh et al., 2001). Serum-deprived PC12 cells were pretreated with the phosphodiesterase inhibitor Ro 20-1724 (5 µM) for 15 min, and stimulated with agonists for 10 min in the presence of Ro 20-1724. The reaction was terminated by addition of 100% EtOH. The samples were centrifuged at 10,000×g for 5 min at 4° C. to remove cell debris. Content of cAMP are measured by competition assay between $^3$H-labeled cAMP and unlabeled cAMP present in the sample, to bind to a crude cAMP binding protein. The binding protein was prepared from bovine adrenal cortex according to the method of Brown et al. (1971). Each sample was incubated with 50 µl $^3$H-labeled cAMP (5 µCi) and 100 µl binding protein for 1 hr at 4° C. Protein-bound cAMP was separated from unbound cAMP via the adsorption of free cAMP onto charcoal (100 µl), followed by centrifugation at 12,000×g at 4° C. The 200 µl supernatant was then placed into an Eppendorf tube containing 1.2 ml scintillation cocktail, in order to measure radioactivity. The cAMP concentration in the sample was determined based on a standard curve.

Reverse Transcriptase—PCR

Total RNA was isolated from cultured PC12 cells using TRIzol™ solution (Invitrogen), and cDNA was synthesized by reverse transcriptase, Superscript II (Invitrogen). The sequences for the KOR primers were as follows: 5'-tggtcatgtttgtcatc-3' (forward) and 5'-catcatcaggaaactgca-3' (reverse). After preheating at 94° C. for 5 min, 30 amplification cycles were performed at 94° C. for 20 s, 53° C. for 20 s, and 72° C. for 30 s. Final incubation was performed at 72° C. for 10 min.

Ligand Binding Analysis

Ligand binding analysis was performed as previously described (Bae et al., 2004). Briefly, PC12 cells were seeded at a density of $4 \times 10^5$ cells/well into a 12-well plate and cultured overnight. After incubating the cells in blocking buffer (33 mM HEPES (pH 7.5) and 0.1% BSA in RPMI 1640) for 2 hr, 25 pM of $^{125}$I-labeled leumorphin dissolved in binding buffer (PBS containing 0.1% BSA) was added to the cells in the absence or presence of unlabeled ligands and incubated for 3 hr at 4° C. The samples were then washed five times with ice-cold binding buffer, and 500 µl of 1 N NaOH was added to each well. After 10 min at room temperature, the lysates were collected and counted using a gamma counter.

Immunoprecipitation

Immunoprecipitation was performed as previously described (Daub et al., 1997). In brief, cells were washed with ice-cold PBS and lysed with lysis buffer (50 mM HEPES pH 7.5, 150 mM NaCl, 1% Triton X-100, 1 mM EDTA, 10% glycerol) containing protease inhibitors (0.5 mM PMSF, 1 µg/ml leupeptin and 5 µg/ml aprotinin) and phosphatase inhibitors (30 mM NaF, 1 mM Na3VO4 and 30 mM Na4O7P2). The cell lysates were incubated for 1 hr at 4° C. After centrifugation (12,000×g for 15 min), equal amounts of soluble extract were incubated for 4 hr, with 5 µg of anti-EGFR antibody and 30 µl of resin volume of immobilized protein G For gel electrophoresis, the precipitates were dissolved in Laemmli sample buffer.

Assay for AKT and ERK Phosphorylation and Western Blot Analysis

Serum-deprived PC12 cells were treated as indicated, washed with ice-cold PBS, and lysed with lysis buffer (50 mM HEPES pH 7.5, 1% Triton X-100, 1 mM EDTA) containing protease inhibitors (0.5 mM PMSF, 1 µg/ml leupeptin and 5 µg/ml aprotinin). The lysates were dissolved in Laemmli sample buffer. Proteins were separated by SDS-PAGE and transferred to a nitrocellulose membrane (Schleicher and Schuell, BA85). Blocking was performed with TBS buffer (10 mM Tris/HCl, pH 7.5, 150 mM NaCl, and 0.05% Tween 20) containing 5% skimmed milk powder. The membrane was probed with the primary antibody as indicated for 3 hr at room temperature. Subsequently the immunoblot was washed and incubated with horseradish peroxidase-linked secondary antibody for 1 hr at room temperature, rinsed four times in TBS buffer, and developed with horseradish peroxidase-dependent chemiluminescence reagents (Amersham International, UK).

TUNEL Assay

TUNEL assay was performed according to the manufactures' instruction (Promega Corp.). Briefly, cells on coverslips were fixed with 4% paraformaldehyde for 30 min after stimulation, washed with PBS, permeabilized with 0.2% Triton X-100 for 5 min, rinsed with PBS, and were incubated with 25 µL TUNEL reaction mixture (containing enzyme, nucleotides, and fluorescein-dUTP) in a humidified atmosphere at 37° C. for 1 hr. To observe nuclear morphology, cells were counterstained with 2 µg/ml propidium iodide. Following these incubations, coverslips were rinsed with PBS three times and analyzed under confocal microscopy We captured images which had at least 100 cells and used five different images from three independent experiments for statistic analysis.

Assay for Caspase-3 Enzymatic Activity

PC12 cell lysates were centrifuged at 1,000×g for 10 min. Equal amount of supernatant (20 µg protein) was diluted in buffer containing 100 mM Hepes, 10% sucrose, 5 mM dithiothreitol, 10-6% NP-40, and 0.1% CHAPS (pH 7.25), and was added to each well of a 96-well plate containing 50 µM DEVD-aminomethylcoumarin (AMC). After incubation at 37° C. for 1 hr, the cleaved free AMC was detected using a fluorospectrophotometer (excitation of 355 nm, emission of 460 nm).

DNA Ploidy Analysis

Cells were suspended in PBS containing 5 mM EDTA and fixed in 100% ethanol. RNase A (50 µg/ml) was added to the suspended cells, and the cells were incubated at room temperature for 30 min. Propidium iodide (2 µg/ml) was added before reading. DNA contents of the cells were analyzed using a FACScan flow cytometer (Becton Dickinson, Franklin Lakes, N.J.), which was also used to determine the percentage of cells in the different phases of the cell cycle.

Statistic Analysis

All experiments, including the immunoblots, were independently repeated a minimum of three times. All immunoblots presented are representative of more than three separate experiments. Quantitative data are expressed as the means±S.E.M. Student's t tests were used where appropriate. A probability of p<0.01 was considered statistically significant.

Example 1

Leumorphin Specifically Regulates Cell Viability in PC12 Cells

Prodynorphin and its cleaved products have been shown to be expressed and secreted from adrenal chromaffin cells and rat pheochromocytoma PC12 cells (Margioris et al., 1992).

FIG. 1A shows a schematic diagram of the prodynorphin precursor and its processed peptides.

Figure 1B:
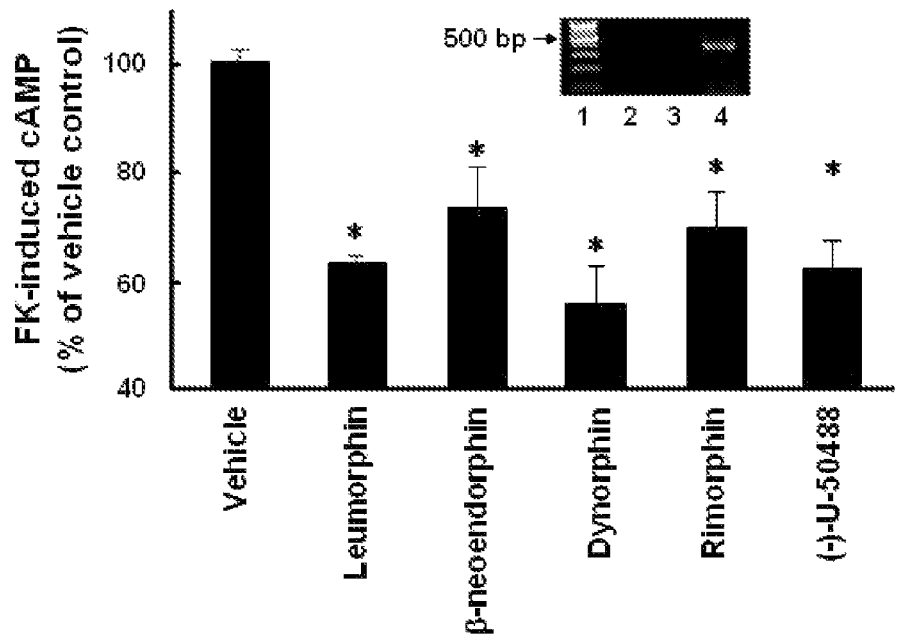

In FIG. 1B, cell death was induced by serum-deprivation, and cell viability was measured by MTT conversion assay after incubating the cells with vehicle or agonists as indicated for 24 hr. All agonists were used at a concentration of 1 µM. Analysis of cell viability by MTT conversion assay was performed as described in "Materials and Methods". Cell viability is presented as a percentage of surviving cells as compared to those at the time of initial serum deprivation.

Figure 1C:
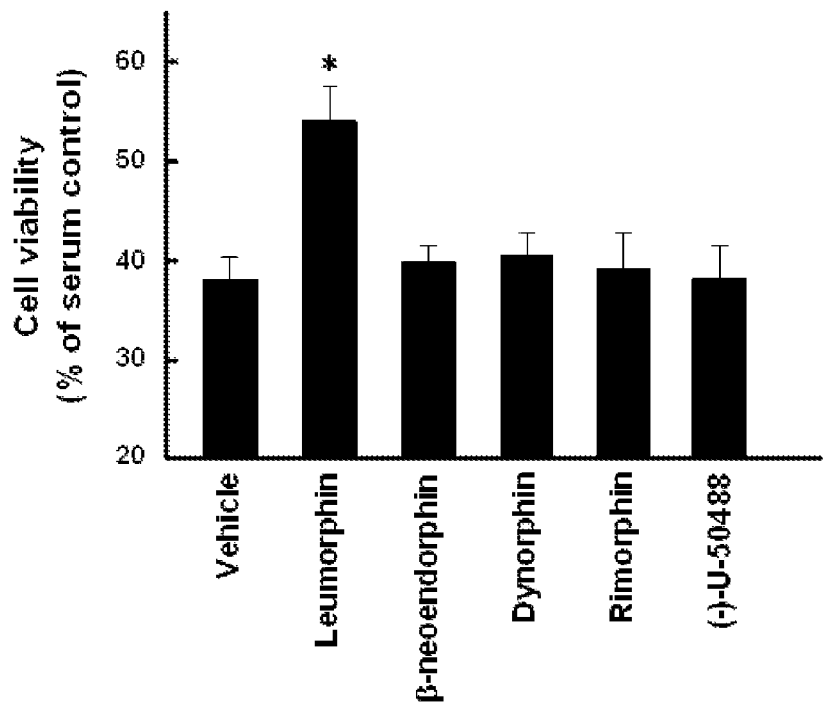

In FIG. 1C, in order to measure changes in cAMP contents, cells were pretreated with Ro-20-1724 (5 µM, 15 min), followed by application of agonists (1 µM) for 10 min in the presence or absence of forskolin (FK). Measurement of cAMP contents was performed as described in "Materials and Methods". Data presented are percent inhibition values as compared to FK-induced cAMP increase without any agonists. Inset shows that PC12 cells express mRNA for KOR, as determined by RT-PCR. Lane 1, DNA size maker; Lane 2, $H_2O$; Lane 3, PCR without the reverse transcriptase; Lane 4, PCR with reverse transcriptase using specific primers for KOR.

Figure 1D:
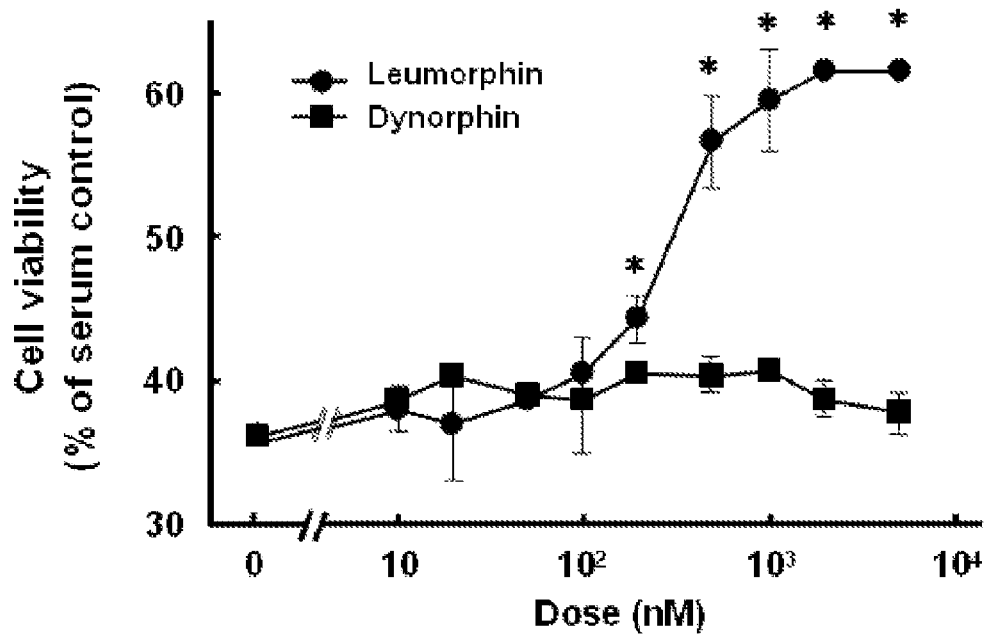
Figure 1E:
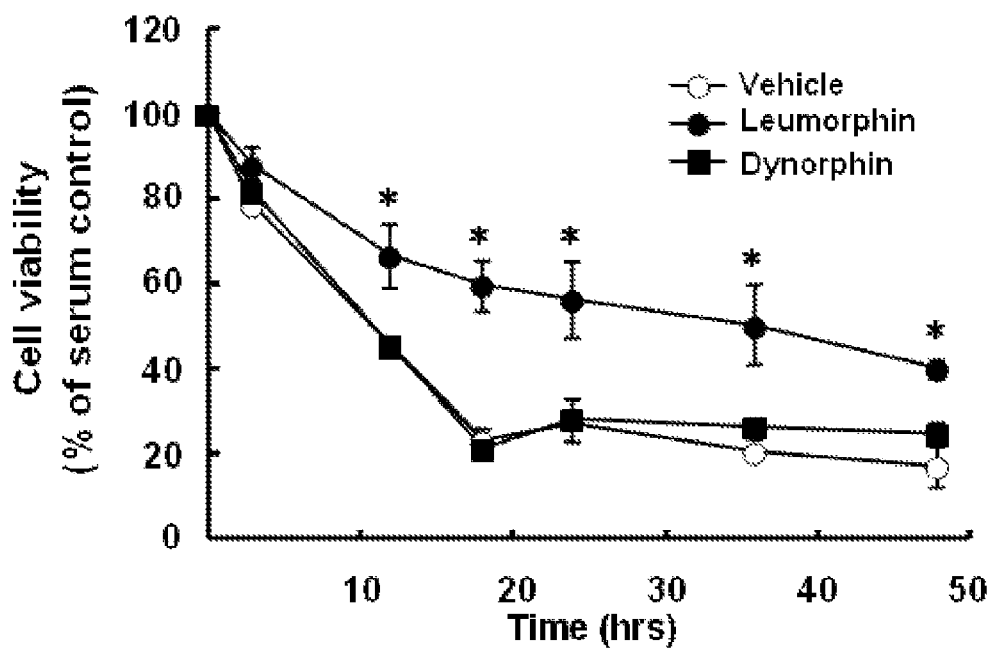

In FIGS. 1D and 1E, cell death was induced by serum-deprivation, and cell viability was measured by MTT assay after incubating the cells with various concentrations of leumorphin and dynorphin for 24 hr (D). Cells were exposed to 1 µM of leumorphin or dynorphin for the indicated times (E). Data shown are the means±S.E.M. from three independent experiments each performed in triplicate. *, p<0.01, represents a significant difference compared to vehicle control.

1-1: Effects of Endogenous Opioid Peptides Derived from Prodynorphin on Cell Viability in PC12 Cells To investigate whether the products of prodynorphin have functional and/or pharmacological differences, we examined the effects of endogenous opioid peptides derived from prodynorphin on cell viability in PC12 cells (FIGS. 1A and 1B). Expression of the K-opioid receptor (KOR) was confirmed by RT-PCR and measurement of cAMP (FIG. 1C), which was in agreement with the previous reports (Kampa et al., 1999; Dermitzaki et al., 2000).

1-2: Effects of the KOR Ligands on Cell Viability

Effects of the KOR ligands on cell viability were investigated by treating them in a condition of serum-deprivation, and MTT conversion assay was performed. Interestingly, cell viability was specifically enhanced by leumorphin, but not by any other endogenous KOR ligands and a specific KOR agonist, (−)-U-50488 (FIG. 1B). KOR is associated with the inhibitory $G\alpha_{i/o}$ family of G proteins which decrease the cAMP production.

As shown in FIG. 1C, all of the KOR ligands tested down-regulated the forskolin-induced increase of cAMP contents, confirming that the KOR ligands we used have proper activities and that functional KOR is expressed in PC12 cells. Besides, there were no significant differences among the KOR ligands in terms of cAMP regulation. The leumorphin-induced enhancement of cell viability occurred in a dose-(FIG. 1D) and a time-dependent (FIG. 1E) manner. To the contrary, dynorphin did not have any significant effect on cell viability (FIG. 1B). These results suggest that leumorphin has a unique function in the regulation of cell viability in PC12 cells.

Example 2

Enhancement of Cell Viability in Response to Leumorphin is Independent of the KOR Activation Cells were treated with vehicle, 1 µM of opioid receptor antagonists (Naloxone, nor-BNI, naltrindole, or CTOP), or 100 ng/ml of PTX as indicated in the presence or absence of leumorphin (1 µM).

Figure 2A:
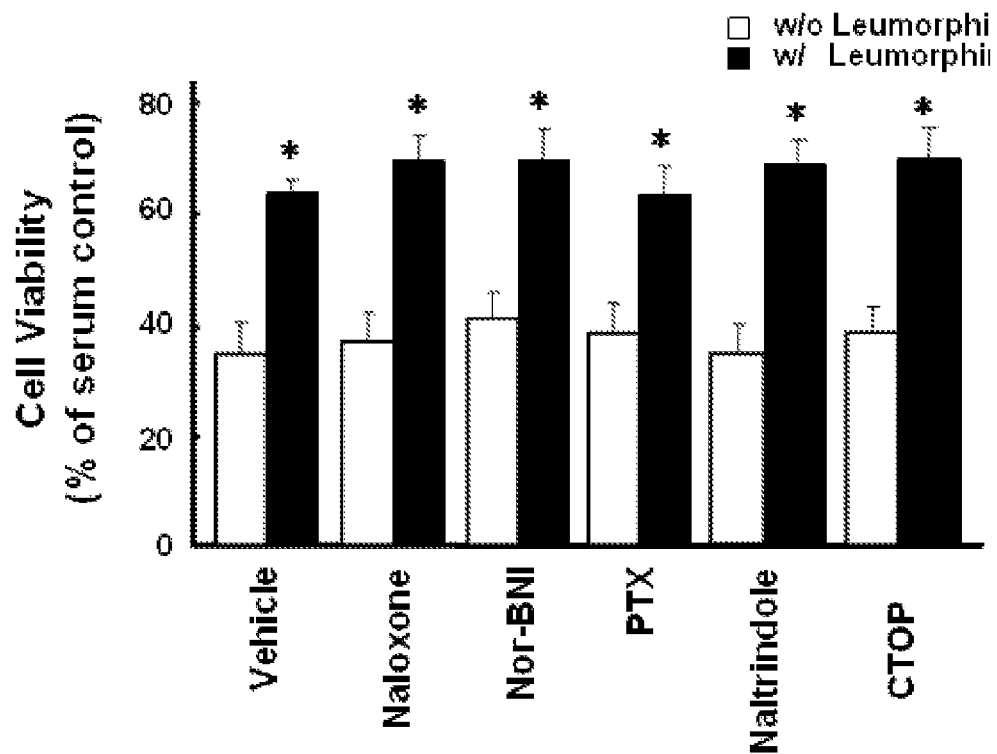
FIGS. 2A and 2B show non-opioid properties of leumorphin in PC12 cells, and cells were treated with vehicle, 1 μM of opioid receptor antagonists (Naloxone, nor-BNI, naltrindole, or CTOP), or 100 ng/ml of PTX as indicated in the presence or absence of leumorphin (1 μM).

In FIG. 2A. MTT conversion assay was performed after 24 hr of treatment as in FIG. 1B.

In FIG. 1B, cells were pretreated with Ro-20-1724 (5 µM, 15 min), followed by application of leumorphin (1 µM, 10 min) in the presence or absence of naloxone or nor-BNI (1 µM). PTX (100 ng/ml) was pretreated for 20 hr. Measurement of cAMP content was performed as in FIG. 1C, and data presented are percent inhibition values as compared to FK-induced cAMP increase without any other drugs. Data shown are the means ±S.E.M. from three independent experiments. *, p<0.01, represents a significant difference compared to vehicle control (w/o leumorphin).

We examined whether the effect of leumorphin on the prevention of cell death was mediated by activation of KOR. As shown in FIG. 2A, the leumorphin-induced enhancement of cell viability was insensitive to both naloxone, a general antagonist of opioid receptor, and nor-BNI, a specific antagonist of the KOR (FIG. 2A). Furthermore, treatment with a specific agonist of the KOR, (−)-U-50488, did not increase cell viability (FIG. 1B).

Figure 2B:
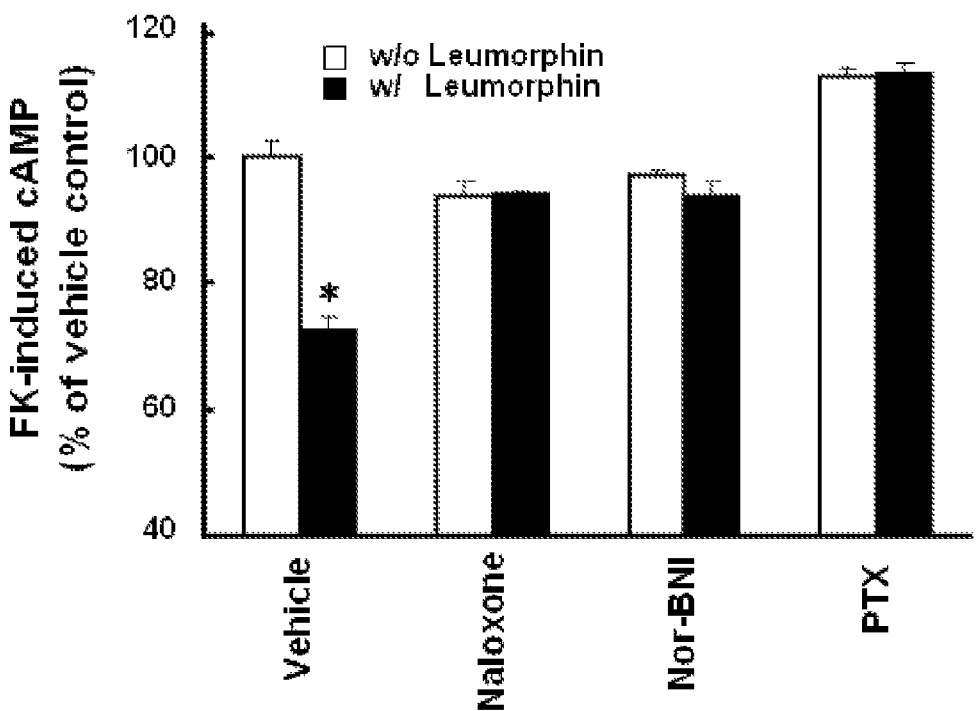

We also examined the effects of higher concentrations of naloxone and nor-BNI (10 µM and 100 µM) on leumorphin-induced increase in cell viability, but both antagonists failed to attenuate the activity elicited by leumorphin even at high concentration (data not shown). Intracellular signaling events downstream of opioid receptor activation are sensitive to pertussis toxin (PTX), because opioid receptors are associated with the $G\alpha_{i/o}$ family of G proteins. However, the leumorphin-induced enhancement of cell viability was unaffected by PTX treatment (FIG. 2A). To the contrary, the inhibitory effect of leumorphin on forskolin-induced increase of cAMP content was reversed by naloxone, nor-BNI and PTX (FIG. 2B). Many opioid peptides do not clearly discriminate the subtype of opioid receptors, but act promiscuously on the µ-opioid receptor (MOR), δ-opioid receptor (DOR), and KOR, though there are selective ligands for each receptor (Waldhoer et al., 2004). To examine whether the increased cell viability induced by leumorphin treatment occurred by its rather non-specific binding to the MOR or DOR, we tested the effects of the DOR and MOR antagonists, naltrindole and CTOP, respectively. Both antagonists failed to attenuate the effect of leumorphin on cell viability (FIG. 2A). Naltrindole and CTOP failed to attenuate the activity elicited by leumorphin even at higher concentration (10 µM and 100 µM) (data not shown).

From these results, we excluded any possible involvement of the DOR and MOR in the leumorphin-induced enhancement of cell viability. Taken together, these results suggest that leumorphin-induced increase in cell viability, which is not manifested by any other prodynorphin gene products, is independent of the KOR activation, i.e., it is mediated by the so-called, non-opioid like action of leumorphin.

Example 3

Leumorphin has a Binding Site(s) in Addition to the Binding Site for the KOR in PC12 Cells We investigated the possibility that leumorphin might have another binding site(s), in addition to the binding site for the KOR in PC12 cells. That is, an inhibition of [$^{125}$I]leumorphin binding in PC12 cells was investigated. PC12 cells were treated with various concentrations of unlabeled leumorphin, (−)-U-50488 and nor-BNI in the presence of $^{125}$I-labeled leumorphin (25 pM) for 3 hr at 4° C. Specifically bound $^{125}$I-labeled leumorphin was measured as described in "Materials and Methods". For this purpose, we performed competition binding assay of $^{125}$I-labeled leumorphin with unlabeled-agonists, leumorphin and (−)-U-50488, and an antagonist, nor-BNI.

As shown in FIG. 3, the extent of inhibition elicited by either (−)-U-50488 or nor-BNI reached up to only 20% of that induced by leumorphin which completely replaced labeled leumorphin at 10 μM. Furthermore, the inhibitory extent of (−)-U-50488 and nor-BNI reached their maximum at 100 nM and was saturated. To the contrary, the inhibitory extent of leumorphin continued to increase up to 10 μM. Therefore, we suggest that this difference might have been resulted from an additional, but unknown binding site for leumorphin in PC12 cells.

Example 4

Leumorphin-Induced Enhancement of Cell Viability is Mediated by AKT and ERK Activation In order to investigate the molecular mechanism underlying the leumorphin-induced enhancement of cell viability, we examined the possible involvement of AKT and ERK, which are essential signaling molecules for the control of cell growth and survival.

For this purpose, we firstly examined whether AKT and/or ERK was activated by leumorphin. Activation of AKT and ERK was monitored by Western blot analysis using phospho-specific antibodies for AKT (p-Ser473) and ERK1/2 (p-Thr202/204), indicative of their activation.

Figure 4A:
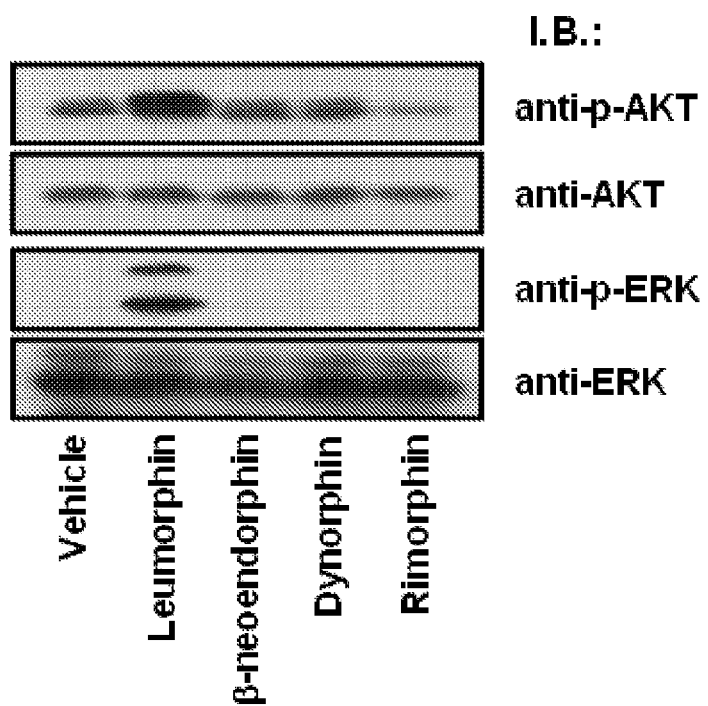
FIG. 4A to 4F show that leumorphin activates AKT and ERK signaling.
Figure 4B:
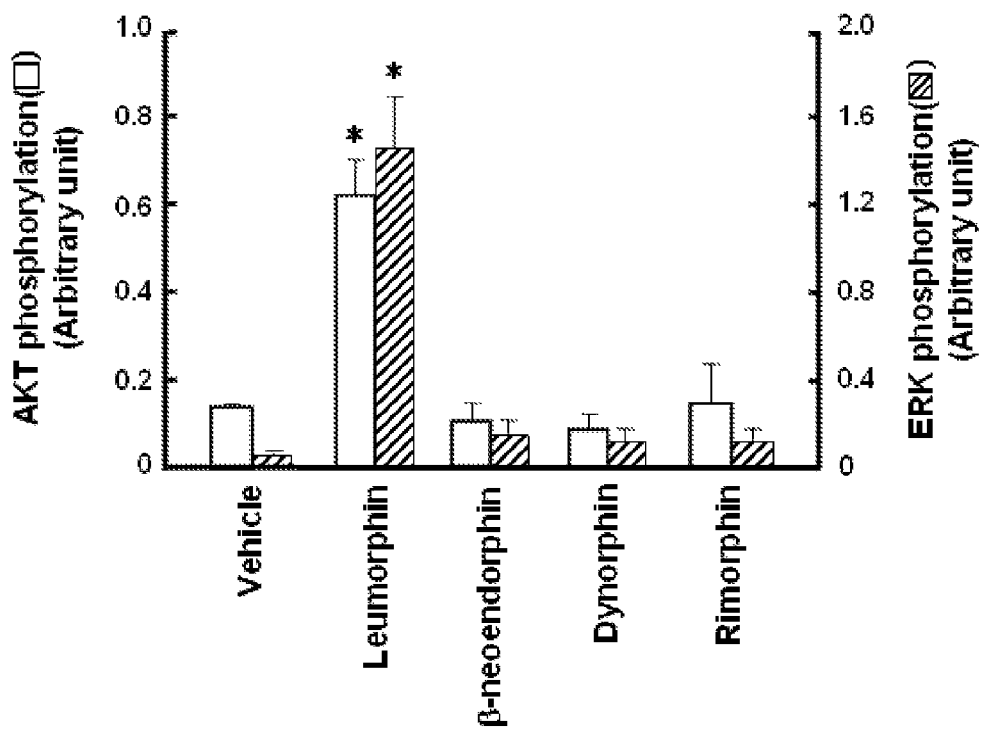
Figure 4C:
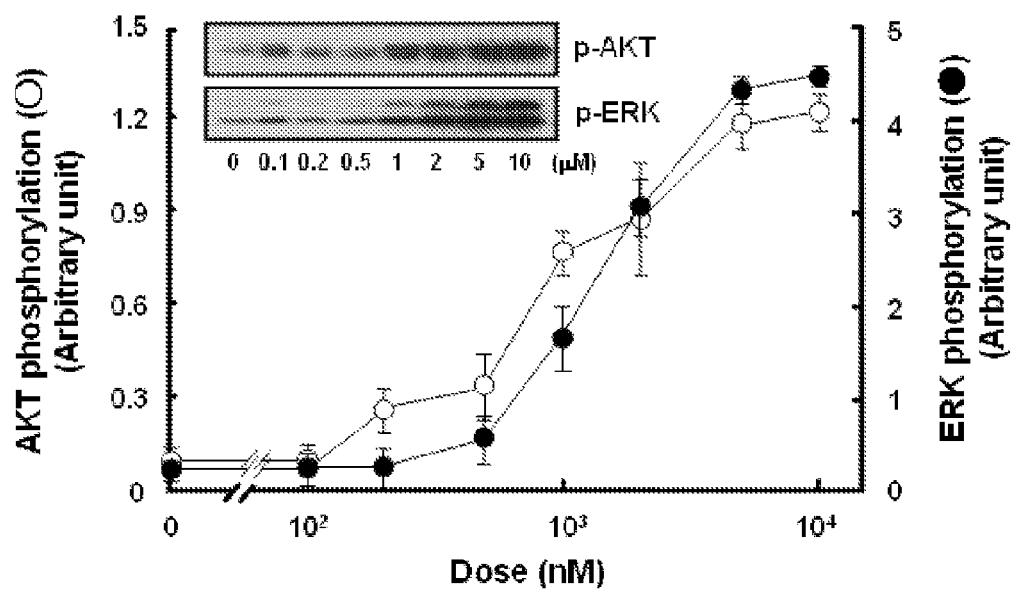
Figure 4D:
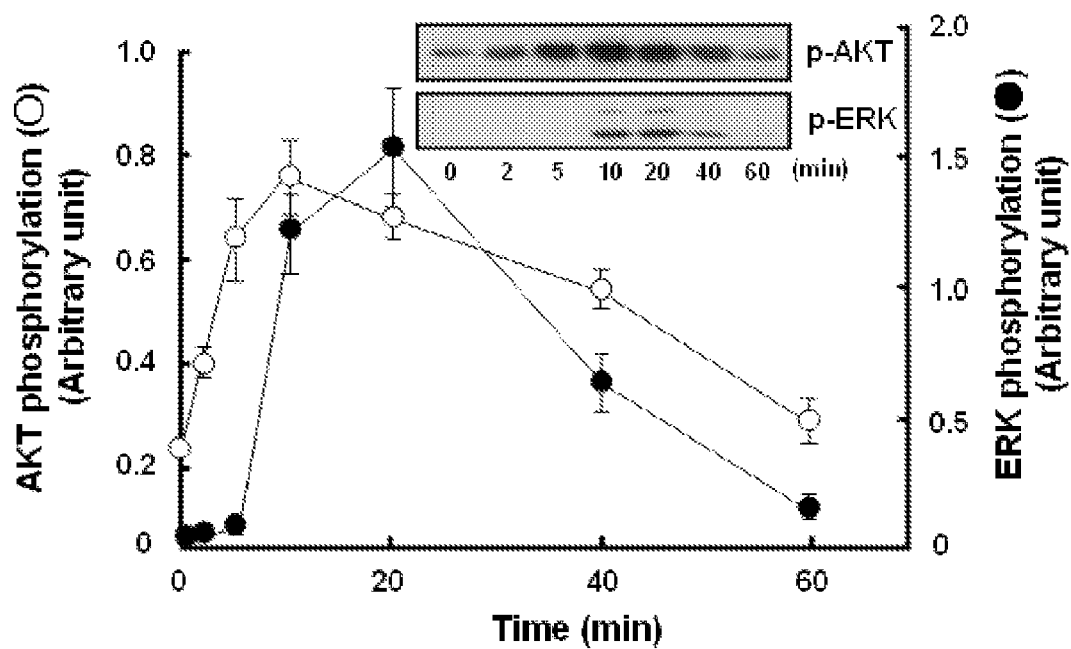
Figure 4E:
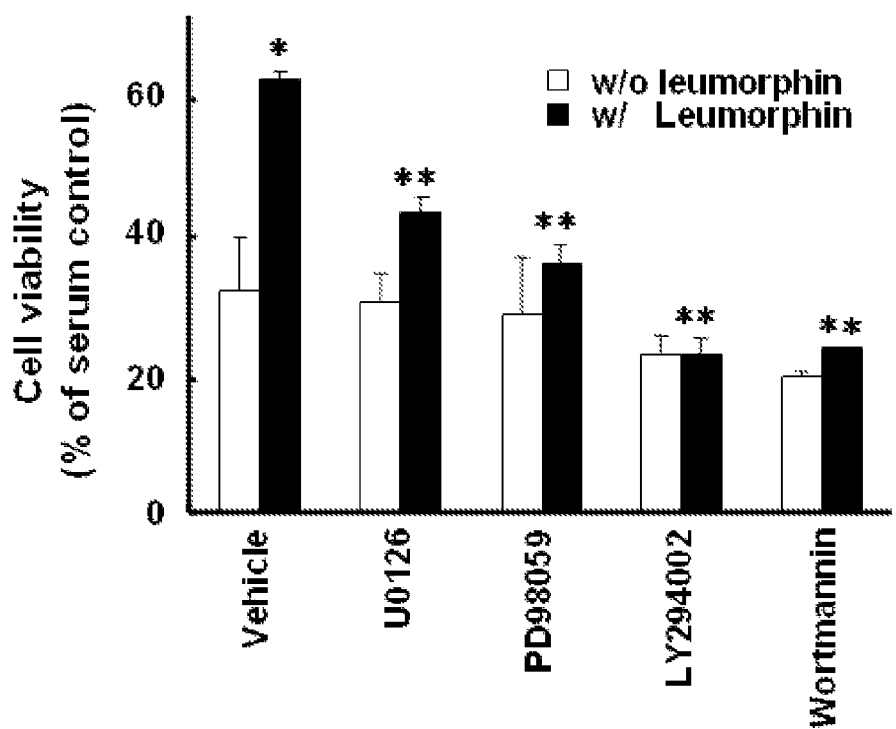
Figure 4F:
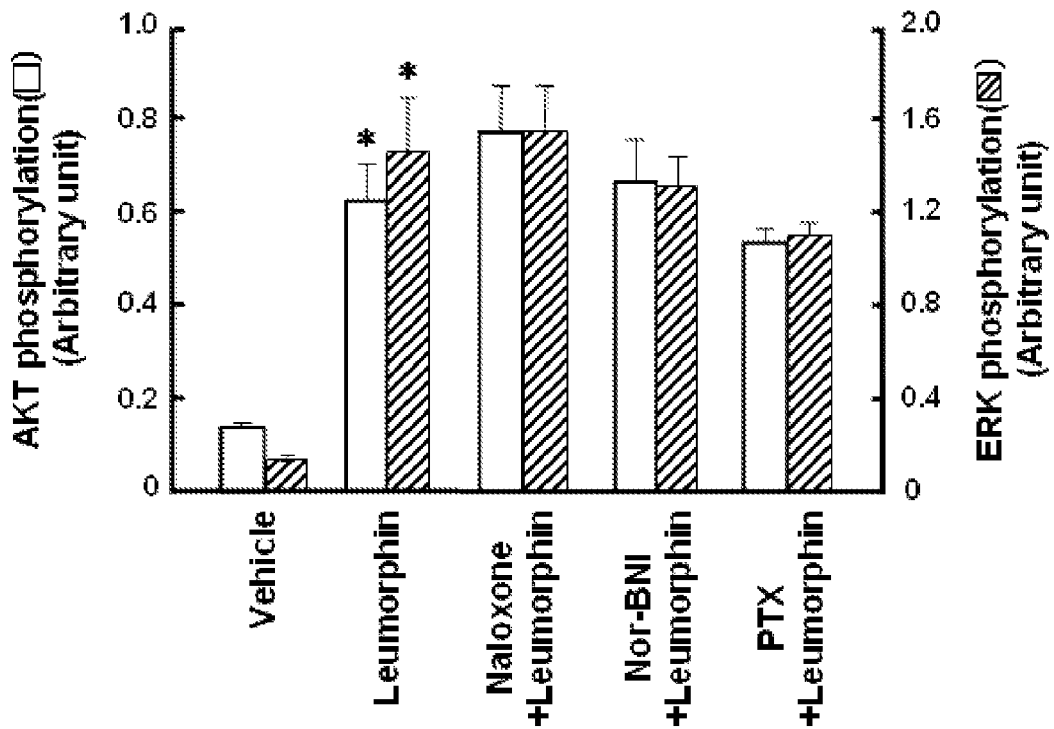

In FIG. 4A, PC12 cells were stimulated with 1 μM of agonists as indicated for 10 min. Western blot analysis was performed to detect phosphorylated AKT and ERK. The amounts of AKT and ERK were monitored by reprobing the same blot with anti-AKT and ERK antibodies. Representative blots from three independent experiments are shown. FIG. 3B shows quantification of AKT and ERK phosphorylation. In FIGS. 4C and 4D, PC12 cells were stimulated with the indicated doses of leumorphin for 10 min (C) or with 1 μM of leumorphin for the indicated times (D). In FIG. 4E, Measurement of cell viability was performed as in FIG. 1B. PC12 cells were incubated with 5 μM of U0126, PD98059, LY294002, or Wortmannin for 24 hr in the presence or absence of 1 μM leumorphin (E). The percentage of surviving cells was calculated as in FIG. 1B. In FIG. 4F, phosphorylation of AKT and ERK was detected by Western blot analysis in the presence or absence of 1 μM opioid receptor antagonists (Naloxone and nor-BNI) or 100 ng/ml PTX.

As shown in FIGS. 4A and B, leumorphin specifically induced phosphorylation of both AKT and ERK, effects which could not be mimicked by any other endogenous KOR ligands. Furthermore, leumorphin but not other prodynorphin gene products specifically induced phosphorylation of AKT and ERK in HEK-293 cells (data not shown) that do not express opioid receptors (Gomes et al. 2002). The mRNA for the KOR was not detected in HEK-293 cells when assessed by RT-PCR (data not shown). The leumorphin-induced phosphorylation of AKT and ERK occurred in a dose—(FIG. 4C) and a time-dependent (FIG. 4D) manner.

In order to investigate whether activation of AKT and ERK was involved in the leumorphin-induced enhancement of cell viability, we examined the effects of P13-Kinase inhibitors, LY294002 and Wortmannin, and inhibitors of MEK, U0126 and PD98059. The leumorphin-induced enhancement of cell viability was attenuated by treatment with inhibitors of PI3-Kinase and MEK (FIG. 4E), suggesting that leumorphin specifically increases cell viability via activation of the PI3-Kinase and MAPK pathways. However, the inactive analogue of U0126, U0124 had no effect (data not shown). Since the effect of leumorphin on cell viability was independent of the KOR activation (FIG. 2A), we examined whether activation of AKT and ERK triggered by leumorphin was also insensitive to opioid antagonists. Neither of the antagonists, naloxone and nor-BNI, inhibited the leumorphin-induced phosphorylation of AKT and ERK. Consistently, PTX did not have any inhibitory effects (FIG. 4F). Nalxone, nor-BNI, and PTX alone did not have any effects on the phosphorylation level of AKT and ERK (data not shown).

Example 5

Leumorphin Enhances Cell Viability and Activates AKT and ERK, in a c-Src- and an Epidermal Growth Factor Receptor (EGFR)-Dependent Manner AKT- and ERK-mediated cell survival signals have been reported to be associated with EGFR activation in many different cell systems (Fischer et al., 2003). We thus investigated whether EGFR activation accounted for the activation of AKT- and ERK-mediated cell survival signals elicited by leumorphin.

Figure 5A:
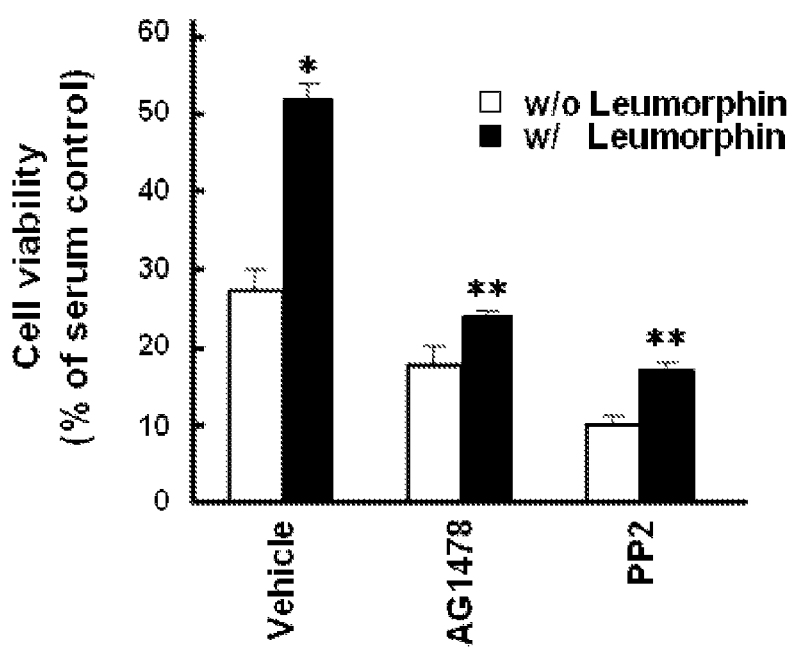
FIG. 5A to 5G show that leumorphin induces Src-dependent EGFR activation in PC12 cells.
Figure 5B:
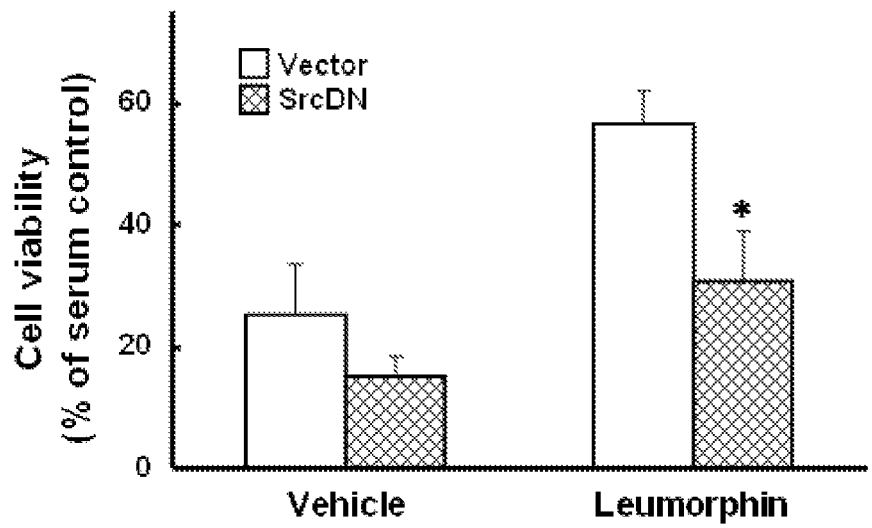

In FIG. 5A, PC12 cells were incubated with 1 μM leumorphin for 24 hr in the presence or absence of 1 μM AG1478 and 5 μM PP2. Cell viability was measured by MTT assay as in FIG. 1B. Data shown are the means±S.E.M. from three independent experiments each performed in triplicate. In FIG. 5B, PC12 cells transiently transfected with either control cDNA (Vector) or dominant negative mutant of Src (SrcDN) were incubated with or without leumorphin (1 μM) for 24 hr. Cell viability was measured by MTT assay as in A. *, p<0.01 represents a significant difference as compared to vector control.

Figure 5C:
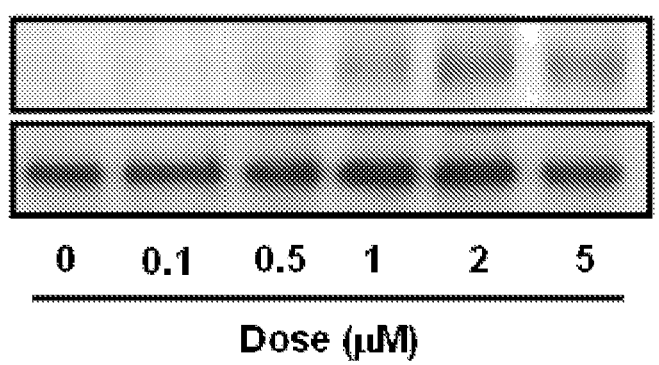
Figure 5D:
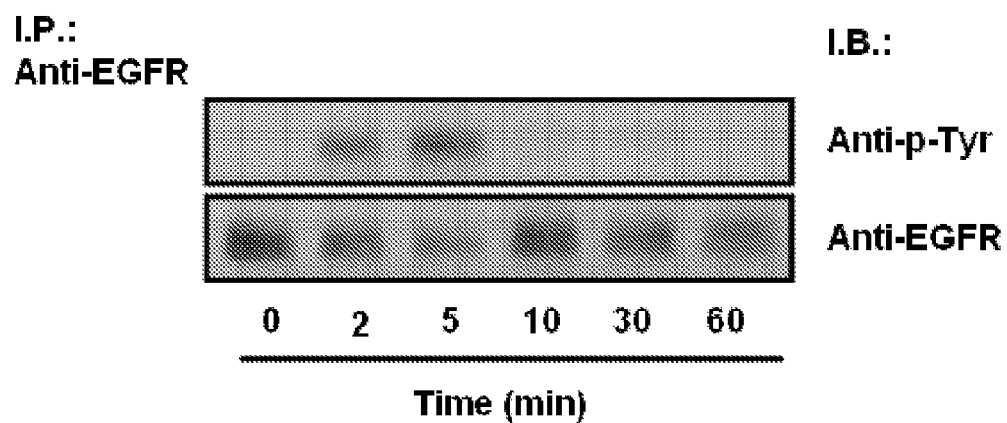
Figure 5E:
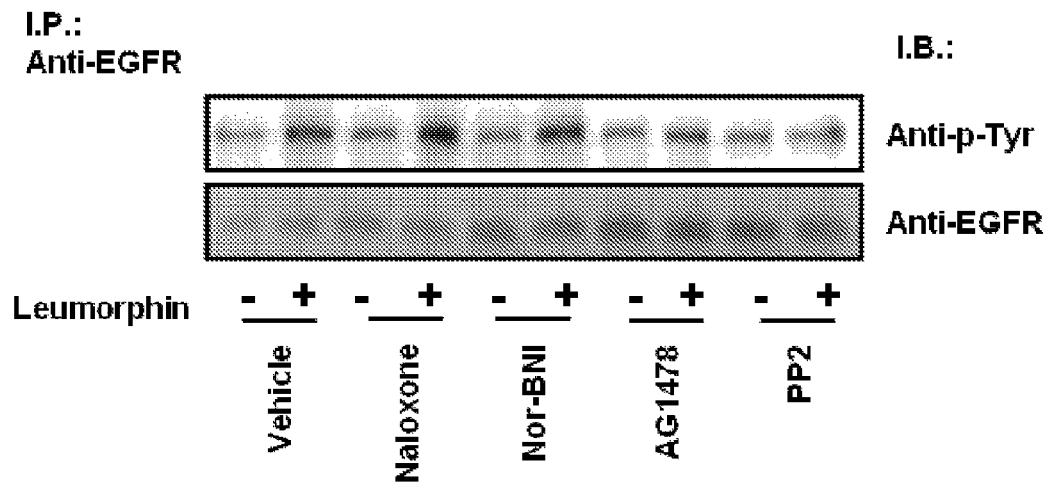
Figure 5F:
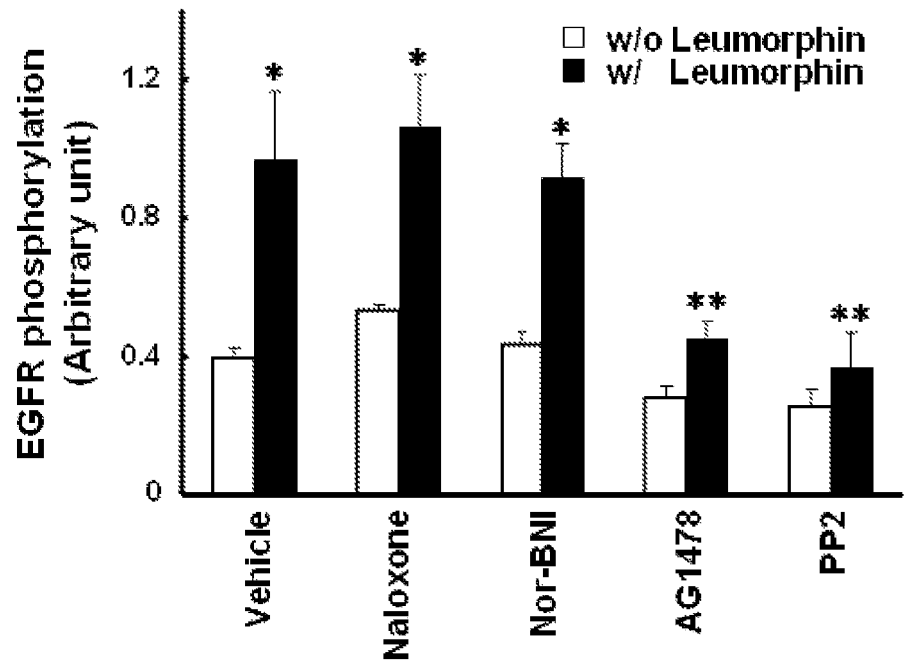
Figure 5G:
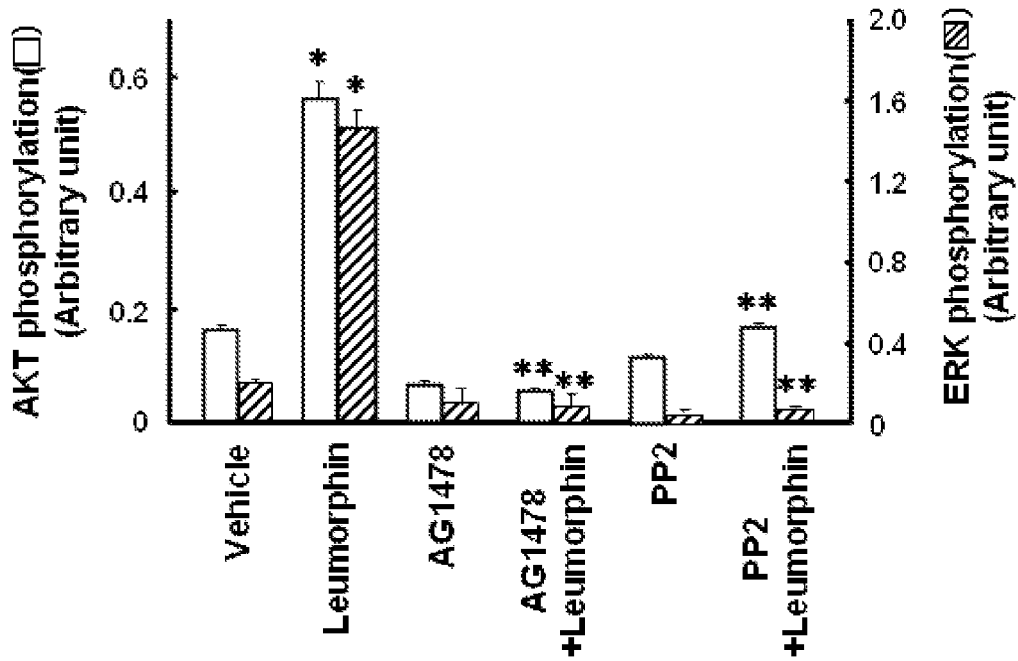

FIGS. 5C and 5D, PC12 cells were stimulated with the indicated doses of leumorphin for 10 min (C) or with 1 μM of leumorphin for the indicated times (D). In FIG. 5E, PC12 cells were preincubated with vehicle, AG1478 (1 μM), PP2 (5 μM), or antagonists (1 μM of naloxone or nor-BNI) for 20 min, followed by 2 min of 1 μM leumorphin treatment. Cell lysates were subjected to Western blot analysis after immunoprecipitation with EGFR antibodies. Tyrosine-phosphorylated EGFRs were detected by immunoblotting with phosphotyrosine antibodies. The amounts of the precipitated EGFRs were monitored by reprobing the same blot with EGFR antibodies. FIG. 5F shows Quantification of FIG. 5E. In FIG. 5G, PC12 cells were preincubated with 1 μM AG1478 or 5 μM PP2 for 20 min and then stimulated with 1 μM leumorphin for 10 min. Phosphorylation of AKT and ERK was detected by Western blot analysis as in FIG. 4F. C-E, As shown in FIG. 5A, AG1478, a specific inhibitor of EGFR kinase, completely blocked the leumorphin-induced increase in cell viability (FIG. 5A) as well as the phosphorylation of AKT and ERK (FIG. 5G). Since Src kinases have been proposed to function as an important intracellular mediator in the EGF-independent EGFR activation, we examined the involvement of Src kinases. The increase in leumorphin-induced cell survival (FIG. 5A) and phosphorylation of AKT and ERK (FIG. 5G) were significantly inhibited by PP2, an inhibitor of Src family kinases.

Furthermore, when kinase-defective mutant of c-Src (SrcDN) (Kitagawa et al., 2002) was transiently transfected, leumorphin-induced enhancement of cell survival response (FIG. 5B) as well as phosphorylation of AKT and ERK (data not shown) were attenuated, indicating that c-Src was critically involved. To ascertain the involvement of EGFR activation, we examined tyrosine phosphorylation of the EGFR, indicative of its activation, after treatment with leumorphin.

As shown in FIGS. 5C and D, leumorphin induced tyrosine phosphorylation of EGFR in dose- and time-dependent manner. Furthermore, leumorphin-induced tyrosine phosphorylation of EGFR was completely blocked to the basal level by AG1478 and PP2. However, neither nor-BNI nor naloxone exhibited any inhibitory effect on the leumorphin-induced tyrosine phosphorylation of EGFR (FIGS. 5E and F). Collectively, these results suggest that the leumorphin-induced up-regulation of cell viability and phosphorylation of AKT and ERK are mediated via activation of Src and EGFR.

Example 6

Leumorphin Exhibits Anti-Apoptotic Effects

It has been reported that in PC12 cells apoptosis can be induced by serum deprivation, which mimics the fluctuations in the supply of growth factors (Batistatou et al., 1993). In order to further investigate the effects of leumorphin on cell survival, we first performed terminal deoxynucleotide transferase-mediated deoxyuridine triphosphate nick end-labeling (TUNEL) assay which detects the status of DNA fragmentation of nuclear DNA. The TUNEL positive cells represent apoptotic cells.

Figure 6A:
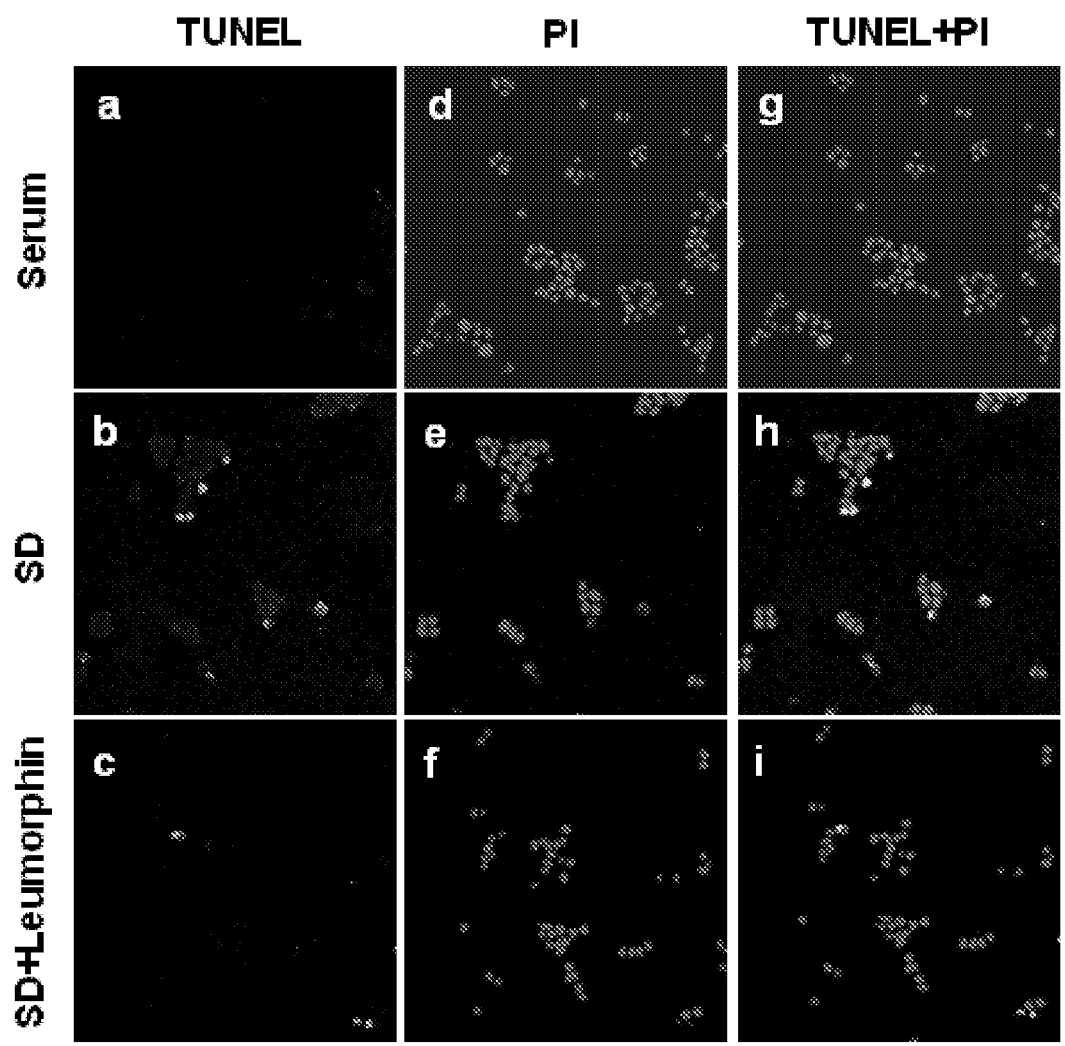
FIG. 6A to 6D represent anti-apoptotic effect of leumorphin in PC12 cells, where PC12 cells were incubated with 1 μM of leumorphin for 24 hr in the presence or absence of 1 μM naloxone or nor-BNI.
Figure 6B:
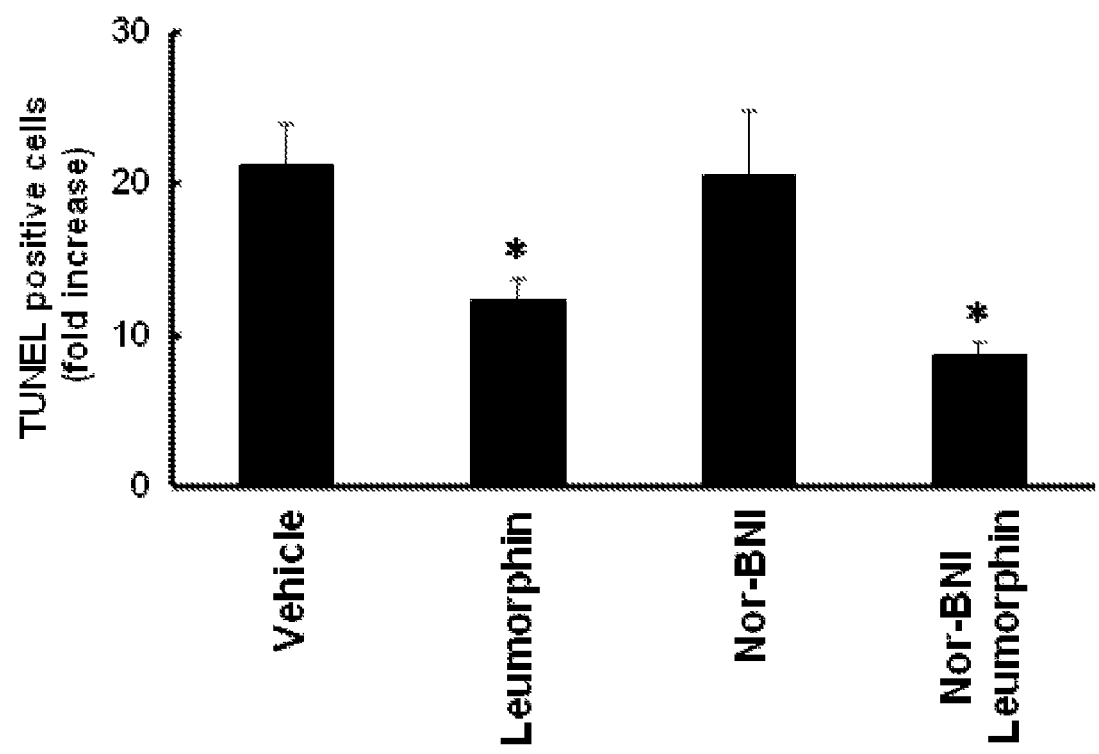
Figure 6C:
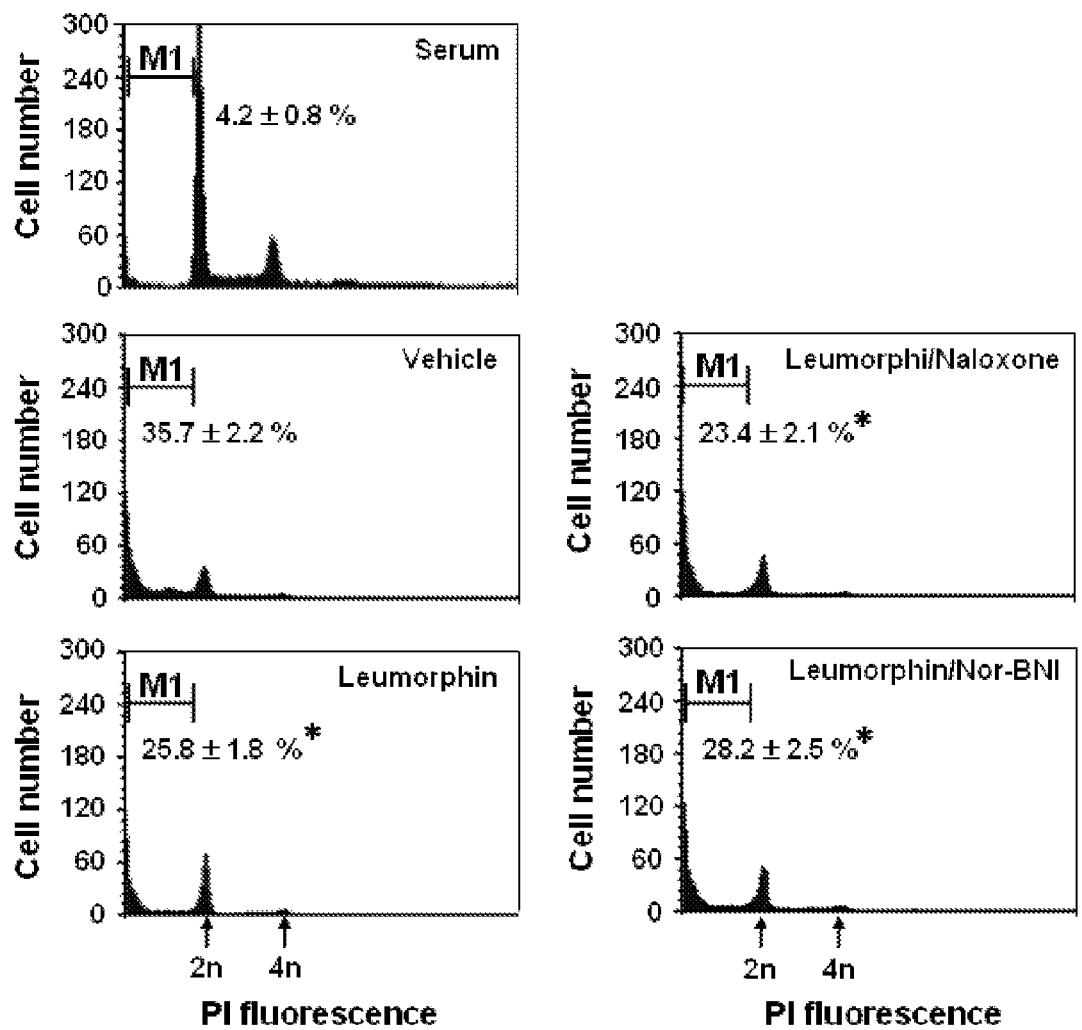
Figure 6D:
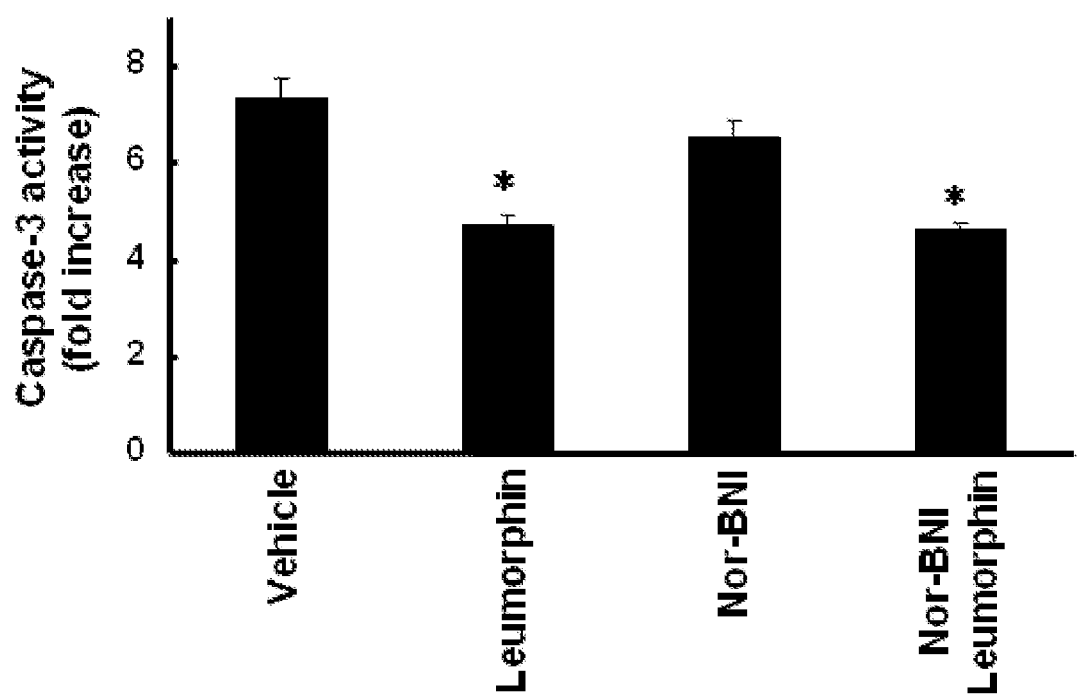

In this example, PC12 cells were incubated with 1 μM of leumorphin for 24 hr in the presence or absence of 1 μM naloxone or nor-BNI. In FIG. 6A, Fragmentation of DNA in the nucleus was detected by a fluorescent TUNEL apoptosis assay. TUNEL stainings are shown in a-c, PI stainings are shown in d-f, and the merged images are presented in g-i. FIG. 6 shows Quantification of the results from TUNEL assay. Each bar represents a fold increase of TUNEL-positive population of cells after treatment as indicated in serum-deprived condition versus those in serum-growing condition. In FIG. 6C, in order to analyze DNA ploidy, cells were fixed with ethanol, and FACS analysis was performed as described in "Materials and Methods". In FIG. 6D, caspase-3 activity was measured by using a specific fluorogenic substrate of caspase-3 (Ac-DEVD -AMC) as described in "Materials and Methods".

As shown in FIGS. 6A and B, leumorphin significantly reduced the population of TUNEL-positive cells, increased by serum deprivation. We next investigated the effect of leumorphin on sub-Go/Gl cell cycle arrest, which can also be an indicator of apoptosis. Loss of DNA is a characteristic marker of cells undergoing apoptosis, which allows discrimination against normal cells. Leumorphin treatment resulted in a reduction of the sub-Go/Gl area, indicative of the apoptotic population, from $35.7\pm2.2\%$ to $25.8\pm1.8\%$ (FIG. 6C). Furthermore, both naloxone and nor-BNI failed to block the anti-apoptotic effect of leumorphin in PC12 cells (FIG. 6C). None of the antagonists significantly affected the cell cycle when administrated alone (data not shown). Furthermore, leumorphin decreased the activity of caspase-3, which was elevated by serum-deprivation (FIG. 6D). The inhibitory effect of leumorphin on caspase activity was not blocked by nor-BNI. Collectively, we provide consistent evidence supporting the notion that leumorphin exerts an anti-apoptotic effect independent of the KOR activation in PC12 cells.

REFERENCES

Arendt R. M., Schmoeckel M., Wilbert-Lampen U., Plasse A., Heucke L., and Werdan K. (1995) Bidirectional effects of endogenous opioid peptides on endothelin release rates in porcine aortic endothelial cell culture: mediating by opioid receptor and opioid receptor antagonist-insensitive mechanisms. J. Pharmacol. Exp. Ther. 272, 1-7.

Bae Y.-S., Lee H. Y, Jo E. J., Kim J. I., Kang H.-I, Ye R D., Kwak J.-Y., and Ryu S. H. (2004) Identification of peptides that antagonize formyl peptide receptor -like 1-mediated signaling. J. Immunol. 173, 607-614.

Batistatou A. and Greene L. A. (1993) Internucleosomal DNA cleavage and neuronal cell survival/death. J. Cell Biol. 122, 523-532.

Berman Y L., Juliano L., and Devi L. A. (1995) Purification and characterization of a dynorphin-processing endopeptidases. J. Biol. Chem. 270, 23845-23850.

Brown B. L., Albano J. D., Ekins R. P., and Sgherzi A. M. (1971) A simple and sensitive saturation assay method for the measurement of adenosine 3:5-cyclic monophosphate. Biochem. J. 121, 561-562.

Cabot P. J., Carter L., and van Winkle D. M. (2001) Methionine-enkephalin and dynorphin A release from immune cells and control of inflammatory pain. Pain 93, 207-212.

Connor M. and Christie M. J. (1999) Opioid receptor signaling mechanisms. Clin. Exp. Pharmacol. Physiol. 26, 493-499.

Daub H., Wallasch C., Lankenau A., Herrlich A., and Ullrich A. (1997) Signal characteristics of G protein-transactivated EGF receptor. EMBO J. 16, 7032-7044.

Dermitzaki E., Chatzaki E., Gravanis A., and Margioris A. N. (2000) Opioid transiently prevent activation of apoptosis mechanisms following short periods of serum withdrawal. J. Neurochem. 74, 960-969.

Fischer O. M., Hart S., Gschwind A., and Ullrich A. (2003) EGFR signal transactivation in cancer cells. Biochem. Soc. T31, 1203-1208.

Gomes I., Filipovska J., Jordan B. A., and Devi, L. A. (2002) Oligomerization of opioid receptors. Methods 27, 358-365.

Gupta K, Kshirsagar S., Chang L., Schwartz R., Law P.-Y., Yee D., and Hebbel R. P. (2002) Morphine stimulates angiogenesis by activating proangiogenic and survival-promoting signaling and promotes breast tumor growth. Cancer Res. 62, 4491-4498.

Hur E. M., Park Y S., Lee B. D., Jang I. H., Kim T. D., Suh P. G, Ryu S. H., and Kim K. T. (2004) Sensitization of epidermal growth factor-induced signaling by bradykinin is mediated by c-Src. Implications for a role of lipid microdomains. J. Biol. Chem. 279, 5852-5860.

Kampa M., Nargioris A. N., Hatzoglou A., Dermitzaki I., Denizot A., Henry J. F., Oliver C., Gravanis A., and Castanas E. (1999) Kappal-opioid binding sites are the dominant opioid binding sites in surgical specimens of human pheochromocytomas and in a human pheochromocytoma (KAT45) cell line. *Eur. J. Pharmacol* 364, 255-62.

Kitagawa D., Tanemura S., Ohata S. et al. (2002) Activation of Extracellular Signal-regulated Kinase by Ultraviolet Is Mediated through Src-dependent Epidermal Growth Factor Receptor Phosphorylation. *J. Biol. Chem.* 277, 366-371.

Luttrell L. M., Della Rocca G. J., van Biesen T., Luttrell D. K., and Lefkowitz R. J. (1997) G□□ Subunits Mediate Src-dependent Phosphorylation of the Epidermal Growth Factor Receptor. A scaffold for G protein-coupled receptor-mediated Ras activation. *J. Biol. Chem.* 272, 4637-4644.

Mansour A., Hoversten M. T., Taylor L. P, Watson S. J., and Akil H. (1995) The cloned μ, δ and κ receptors and their endogenous ligands: Evidence for two opioid peptide recognition cores. *Brain Res.* 700, 89-98.

Margioris A. N., Markogiannakis E., Markrigiannakis A., and Gravanis A. (1992) PC12 rat pheochromocytoma cells synthesize dynorphin. Its secretion is modulated by nicotine and nerve growth factor. *Endocrinol.* 131, 703-9.

Minami M. and Satoh M. (1995) Molecular biology of the opioid receptors: structures, dunctions and distributions. *Neurosci. Res.* 23, 121-145.

Mollereau C., Simons M. J., Soularue P., Liners F, Vassart G, Meunier J. C., and Parmentier M. (1996) Structure, tissue distribution, and chromosomal localization of the prepreonociceptin gene. *Proc. Natl. Acad. Sci. USA* 93, 8666-8670.

Moon T. D. (1988) The effect of opiates upon prostatic carcinoma cell growth. *Biochem. Biophys. Res. Commun.* 153, 722-727.

Mosmann T. (1983) Rapid colorimetric assay for cellular growth and survival: application to proliferation and cytotoxicity assays. *J. Immunol. Methods* 65, 55-63.

Navolotskaya E. V, Malkova N. V., Zargarova T. A., Lepikhova T. N., Zav'yalov V P., and Lipkin V. M. (2002) Synthetic peptide SLTCLVKGFY compete with □-endorphin for nalxone-insensitive binding sites on rat brain membrances. *Peptides* 23, 1115-1119.

Nock B., Giordano A. L., Cicero T. J., and O'connor L. H. (1990) Affinity of drugs and peptides for U-69,593-sensitive κ opioid binding site: The U69,593-insensitive sites appears to be the □-endorphin-specific ε receptor. *J. Pharmacol. Exp. Ther.* 254, 412-419.

Persson A. I., Thorlin T., Bull C., and Eriksson P. S. (2003) Opioid-induced proliferation through the MAPK pathway in cultures of adult hippocampal progenitors. *Mol. Cell. Neurosci.* 23, 360-372.

Polakiewicz R. D., Schieferl S. M., Gingras A. C., Sonenberg N., and Comb M. J. (1998) mu-opioid receptor activates signaling pathways implicated in cell survival and translational control. *J. Biol. Chem.* 273, 23534-23541.

Redell J. B., Moore A. N., and Dash P. K. (2003) Expression of the prodynorphin gene after experimental brain injury and its role in behavioral dysfunction. *Exp. Bio. Med.* 228, 261-269.

Singh I. N., Goody R. J., Goebel S. M. et al. (2003) Dynorphin A (1-17) induces apoptosis in striatal neurons in vitro through alpha-amino-3-hydroxy-5-methylisoxazole-4-propionate/kainate receptor-mediated cytochrome c release and caspase-3 activation. *Neurosci.* 122, 1013-23.

Solbrig M. V. and Koob G. G. (2004) Epilepsy, CNS viral injury and dynorphin. *TRENDS Pharmacol. Sci.* 25, 98-104.

Suda M., Nakao K., Yoshimasa T., Ikeda Y., Sakamoto M., Yahaihara N., Numa S., and Imura H. (1983a) A novel opioid peptide, leumorphin, acts as an agonist at the κ opiate receptor. *Life Sci.* 32, 2769-2775.

Suda T., Tozawa F., Tachibana S., Demura H., Shizume K., Sasaki A., Mouri T., and Miura Y (1983b) Multiple forms of immunoreactive dynorphin in human pituitary and pheochromocytoma. *Life Sci.* 32, 865-70.

Suh B. C., Lee H., Jun D. J., Chun J. S., Lee J. H., and Kim K. T. (2001) Inhibition of H2 histamine receptor-mediated cation channel opening by protein kinase C in human promyelocytic cells. *J. Immunol.* 167, 1663-1671.

Tan-No K., Cebers G, Yakovleva T. et al. (2001) Cytotoxic effects of dynorphins through nonopioid intracellular mechanisms. *Exp. Cell Res.* 269, 54-63.

Tegerder I. and Geisslinger G (2004) Opioids as modulators of cell death and survival-unraveling mechanisms and revealing new indications. *Pharmacol. Rev* 56, 351-369.

Waldhoer M., Bartlett S. E., and Whistler J. L. (2004) Opioid receptors. *Ann. Rev Biochem.* 73, 953-990.

Walker J. M., Moises H. C., Coy D. H., Baldrighi G, and Akil H. (1982) Nonopiate effects of dynorphin and des-tyr-dynorphin. *Science* 22, 623-630.

Wollemann M. and Benyhe S. (2004) Non-opioid actions of opioid peptides. *Life Sci.* 75, 257-270.

Yoshikawa M., Nakayama H., Ueno S., Nishimine N., and Furuya H. (2001) Novel quantitative reverse-transcribed polymerase chain reaction of mu opioid receptor mRNA level. *Brain Res. Protocols* 7, 147-153.

Yoshimasa T., Nakao K., Oki S., Tanaka I., Nakai Y, and Imura H. (1981) Presence of dynorphin-like immunoreactivity in pheochromocytomas. *J. Clin. Endocrinol. Metab.* 53, 213-14.

Zagon I. S., Gibo D. M., and McLaughlin P. J. (1991) Zeta (ζ), a growth-related opioid receptor in developing rat cerebellum: identification and charterization. *Brain Res.* 551, 28-35.

What is claimed is:

1. A method of inhibiting cell apoptosis in a subject at risk for damage to blood vessels or tissue organs caused at least in part by apoptosis, said method consisting of
administering to the subject, a dose of leumorphin as an active ingredient in a sufficient amount to inhibit cell apoptosis.

2. The method according to claim 1, wherein the leumorphin activates epidermal growth factor receptor kinase (ERK) and a protein kinase B (AKT).

3. The method according to claim 1, wherein said subject has been identified as suffering from sepsis, ischemia/reperfusion injury, stroke, ischemic stroke, acute myocardial infarction, acute neurodegenerative disease, chronic neurodegenerative disease, organ transplantation, chemotherapy or brain radiation injury.

* * * * *